(12) United States Patent
Kuramochi et al.

(10) Patent No.: US 10,435,458 B2
(45) Date of Patent: Oct. 8, 2019

(54) ANTIBODY CONSTANT REGION VARIANTS WITH REDUCED FCGAMMAR BINDING

(75) Inventors: Taichi Kuramochi, Shizuoka (JP); Tomoyuki Igawa, Shizuoka (JP); Atsuhiko Maeda, Shizuoka (JP); Futa Mimoto, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/582,073

(22) PCT Filed: Mar. 4, 2011

(86) PCT No.: PCT/JP2011/055101
§ 371 (c)(1),
(2), (4) Date: Dec. 20, 2012

(87) PCT Pub. No.: WO2011/108714
PCT Pub. Date: Sep. 9, 2011

(65) Prior Publication Data
US 2013/0101581 A1   Apr. 25, 2013

(30) Foreign Application Priority Data
Mar. 4, 2010 (JP) .................. 2010-048218

(51) Int. Cl.
*C07K 16/30* (2006.01)
*C07K 16/28* (2006.01)
*C07K 16/18* (2006.01)
*C07K 19/00* (2006.01)
*C07K 16/00* (2006.01)

(52) U.S. Cl.
CPC ........ *C07K 16/00* (2013.01); *C07K 2317/522* (2013.01); *C07K 2317/524* (2013.01); *C07K 2317/71* (2013.01); *C07K 2317/72* (2013.01)

(58) Field of Classification Search
None
See application file for complete search history.

(56) References Cited

U.S. PATENT DOCUMENTS

| | | |
|---|---|---|
| 5,126,250 A | 6/1992 | McDonough et al. |
| 5,322,678 A | 6/1994 | Morgan et al. |
| 5,639,641 A | 6/1997 | Pedersen et al. |
| 5,670,373 A | 9/1997 | Kishimoto |
| 5,795,965 A | 8/1998 | Tsuchiya et al. |
| 5,859,205 A | 1/1999 | Adair et al. |
| 5,945,311 A | 8/1999 | Lindhofer et al. |
| 5,990,286 A | 11/1999 | Khawli et al. |
| 6,126,980 A | 10/2000 | Smith et al. |
| 6,329,511 B1 | 12/2001 | Vasquez et al. |
| 6,485,943 B2 | 11/2002 | Stevens et al. |
| 6,677,436 B1 | 1/2004 | Sato et al. |
| 6,723,319 B1 | 4/2004 | Ito et al. |
| 6,884,879 B1 | 4/2005 | Baca et al. |
| 6,913,747 B1 | 7/2005 | Co et al. |
| 7,052,873 B2 | 5/2006 | Tsuchiya |
| 7,122,637 B2 | 10/2006 | Presta |
| 7,217,797 B2 | 5/2007 | Hinton et al. |
| 7,276,585 B2 | 10/2007 | Lazar et al. |
| 8,062,635 B2 | 11/2011 | Hattori et al. |
| 8,592,562 B2 | 11/2013 | Kannan et al. |
| 9,096,651 B2 | 8/2015 | Igawa et al. |
| 9,150,663 B2 | 10/2015 | Labrijn et al. |
| 9,228,017 B2 | 1/2016 | Igawa et al. |
| 9,670,269 B2 | 6/2017 | Igawa et al. |
| 9,688,762 B2 | 6/2017 | Igawa et al. |
| 10,011,858 B2 | 7/2018 | Igawa et al. |
| 10,066,018 B2 | 9/2018 | Igawa et al. |
| 10,150,808 B2 | 12/2018 | Kuramochi et al. |
| 10,253,091 B2 | 4/2019 | Igawa et al. |
| 2001/0001663 A1 | 5/2001 | Kishimoto et al. |
| 2002/0142374 A1 | 10/2002 | Gallo et al. |
| 2002/0147326 A1 | 10/2002 | Chaiklin et al. |
| 2002/0164339 A1 | 11/2002 | Do et al. |
| 2002/0164668 A1 | 11/2002 | Durham et al. |
| 2002/0187150 A1 | 12/2002 | Mihara et al. |
| 2003/0190311 A1 | 10/2003 | Dall'Acqua et al. |
| 2003/0224397 A1 | 12/2003 | Lowman et al. |
| 2004/0071706 A1 | 4/2004 | Ito et al. |
| 2004/0081651 A1 | 4/2004 | Karpusas et al. |
| 2004/0236080 A1 | 11/2004 | Aburatani et al. |
| 2005/0095243 A1 | 5/2005 | Chan et al. |
| 2005/0130224 A1 | 6/2005 | Saito et al. |
| 2005/0142133 A1 | 6/2005 | Lazar et al. |

(Continued)

FOREIGN PATENT DOCUMENTS

| | | |
|---|---|---|
| CA | 2 203 182 | 5/1996 |
| CA | 2 443 294 | 10/2002 |

(Continued)

OTHER PUBLICATIONS

Paul, Fundamental Immunology, 3rd Edition, 1993, pp. 292-295.*
Bendig M. M. (Methods: A Companion to Methods in Enzymology, 1995; 8:83-93).*
Ward (Nature, vol. 341, p. 544-546, 1989).*
Presta, "Engineering of therapeutic antibodies to minimize immunogenicity and optimize function," *Adv. Drug Deliv. Rev.*, 58(5-6):640-56 (2006).
USPTO Restriction Requirement in U.S. Appl. No. 12/680,082, dated Jun. 6, 2012, 12 pages.

(Continued)

*Primary Examiner* — Michael Allen
(74) *Attorney, Agent, or Firm* — Fish & Richardson P.C.

(57) ABSTRACT

The present inventors carried out dedicated research to generate antibody constant regions with reduced Fcγ receptor-binding activity by altering amino acid sequences in the antibody constant region. As a result, the present inventors successfully identified novel constant region sequences with reduced Fcγ receptor-binding activity compared to conventional antibody constant regions.

2 Claims, 8 Drawing Sheets
Specification includes a Sequence Listing.

(56) References Cited

U.S. PATENT DOCUMENTS

| | | |
|---|---|---|
| 2005/0142635 A1 | 6/2005 | Tsuchiya et al. |
| 2005/0191293 A1 | 9/2005 | Deshpande et al. |
| 2005/0244403 A1 | 11/2005 | Lazar et al. |
| 2005/0261229 A1 | 11/2005 | Gillies et al. |
| 2006/0019342 A1 | 1/2006 | Dall Acqua et al. |
| 2006/0024298 A1* | 2/2006 | Lazar et al. ............... 424/133.1 |
| 2006/0063228 A1 | 3/2006 | Kasaian et al. |
| 2006/0074225 A1 | 4/2006 | Chamberlain |
| 2006/0134709 A1 | 6/2006 | Stavenhagen et al. |
| 2006/0160184 A1 | 7/2006 | Hoogenboom et al. |
| 2006/0194280 A1 | 8/2006 | Dillon et al. |
| 2006/0204493 A1 | 9/2006 | Huang et al. |
| 2006/0275282 A1 | 12/2006 | Moore et al. |
| 2006/0292147 A1 | 12/2006 | Yoshizaki et al. |
| 2007/0036785 A1 | 2/2007 | Kishimoto et al. |
| 2007/0036799 A1 | 2/2007 | Stavenhagen et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0110757 A1 | 5/2007 | Wei et al. |
| 2007/0134234 A1 | 6/2007 | Smith et al. |
| 2007/0148163 A1 | 6/2007 | Takahashi et al. |
| 2007/0148164 A1* | 6/2007 | Farrington ............. C07K 16/00 424/133.1 |
| 2008/0063635 A1 | 3/2008 | Takahashi et al. |
| 2008/0166756 A1 | 7/2008 | Tsuchiya et al. |
| 2009/0208416 A1 | 8/2009 | Moretta et al. |
| 2009/0221803 A1 | 9/2009 | Dall'Acqua et al. |
| 2009/0263392 A1 | 10/2009 | Igawa et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0239577 A1 | 9/2010 | Igawa et al. |
| 2010/0286374 A1 | 11/2010 | Kannan et al. |
| 2010/0291072 A1 | 11/2010 | Lowman et al. |
| 2010/0298542 A1 | 11/2010 | Igawa et al. |
| 2010/0331527 A1 | 12/2010 | Davis et al. |
| 2011/0076275 A1 | 3/2011 | Igawa et al. |
| 2011/0129459 A1 | 6/2011 | Kuramochi et al. |
| 2011/0236374 A1 | 9/2011 | Shitara et al. |
| 2011/0245473 A1 | 10/2011 | Igawa et al. |
| 2011/0287009 A1 | 11/2011 | Scheer et al. |
| 2012/0009188 A1 | 1/2012 | Behrens |
| 2012/0010387 A1 | 1/2012 | Niwa et al. |
| 2012/0028304 A1 | 2/2012 | Dahiyat et al. |
| 2012/0065379 A1 | 3/2012 | Igawa et al. |
| 2012/0071634 A1 | 3/2012 | Igawa et al. |
| 2012/0149876 A1 | 6/2012 | Von Kreudenstein |
| 2012/0238729 A1 | 9/2012 | Kuramochi et al. |
| 2013/0011866 A1 | 1/2013 | Igawa et al. |
| 2013/0018174 A1 | 1/2013 | Igawa et al. |
| 2013/0030156 A1 | 1/2013 | Apostolou et al. |
| 2013/0039913 A1 | 2/2013 | Labrijn et al. |
| 2013/0052196 A1 | 2/2013 | Apostolou et al. |
| 2013/0085199 A1 | 4/2013 | Tamori et al. |
| 2013/0115208 A1 | 5/2013 | Ho et al. |
| 2013/0195849 A1 | 8/2013 | Spreter et al. |
| 2014/0112883 A1 | 4/2014 | Ponath et al. |
| 2014/0303356 A1 | 10/2014 | Gramer et al. |
| 2014/0377253 A1 | 12/2014 | Harding et al. |
| 2015/0118184 A1 | 4/2015 | Kawai |
| 2015/0274809 A1 | 10/2015 | Igawa et al. |
| 2015/0284465 A1 | 10/2015 | Igawa et al. |
| 2015/0315278 A1 | 11/2015 | Igawa et al. |
| 2016/0159915 A1 | 6/2016 | Igawa et al. |
| 2016/0229915 A1 | 8/2016 | Igawa et al. |
| 2017/0275332 A1 | 9/2017 | Igawa et al. |
| 2017/0283483 A1 | 10/2017 | Igawa et al. |
| 2018/0142027 A1 | 5/2018 | Igawa et al. |
| 2018/0162902 A1 | 6/2018 | Igawa et al. |
| 2019/0062368 A1 | 2/2019 | Igawa et al. |

FOREIGN PATENT DOCUMENTS

| | | |
|---|---|---|
| CA | 2 523 577 | 11/2004 |
| CA | 2 531 482 | 1/2005 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 647 846 | 10/2007 |
| CA | 2 700 986 | 4/2009 |
| CN | 101198698 | 6/2008 |
| CN | 102471378 | 5/2012 |
| CN | 102782131 | 11/2012 |
| CN | 102946906 | 2/2013 |
| EP | 0 329 185 | 4/1994 |
| EP | 0 637 593 | 2/1995 |
| EP | 0 783 893 | 7/1997 |
| EP | 0 811 691 | 12/1997 |
| EP | 1 069 185 | 1/2001 |
| EP | 1 510 943 | 3/2005 |
| EP | 1 701 979 | 9/2006 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 900 814 | 3/2008 |
| EP | 2 006 381 | 12/2008 |
| EP | 2 009 101 | 12/2008 |
| EP | 2 031 064 | 3/2009 |
| EP | 2 107 115 | 10/2009 |
| EP | 2 194 066 | 6/2010 |
| EP | 2 196 541 | 6/2010 |
| EP | 2 202 245 | 6/2010 |
| EP | 2 206 775 | 7/2010 |
| EP | 2 236 604 | 10/2010 |
| EP | 2 409 991 | 1/2012 |
| EP | 2 522 724 | 11/2012 |
| EP | 2 543 727 | 1/2013 |
| EP | 2 644 698 | 10/2013 |
| EP | 2 905 290 | 8/2015 |
| EP | 2 914 634 | 9/2015 |
| JP | 2-028200 | 1/1990 |
| JP | H03-500644 | 2/1991 |
| JP | 07-67688 | 3/1995 |
| JP | H08-500979 | 2/1996 |
| JP | H09-506001 | 6/1997 |
| JP | 11-500916 | 1/1999 |
| JP | H11-500915 | 1/1999 |
| JP | 2002-514406 | 5/2002 |
| JP | 2004-086862 | 3/2004 |
| JP | 2004-511426 | 4/2004 |
| JP | 2005-501514 | 1/2005 |
| JP | 2005-101105 | 3/2005 |
| JP | 2005-535341 | 11/2005 |
| JP | 2005-378266 | 12/2005 |
| JP | 2005-537009 | 12/2005 |
| JP | 2008-512995 | 5/2008 |
| JP | 2008-523140 | 7/2008 |
| JP | 2008-538920 | 11/2008 |
| JP | 2009-500458 | 1/2009 |
| JP | 2010-522701 | 7/2010 |
| JP | 2011-508604 | 3/2011 |
| JP | 2012-510281 | 5/2012 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 5334319 | 11/2013 |
| JP | 5484060 | 5/2014 |
| JP | 2015-510764 | 4/2015 |
| JP | 5717624 | 5/2015 |
| JP | 2015-130883 | 7/2015 |
| JP | 5787446 | 9/2015 |
| JP | 2016-69329 | 5/2016 |
| KR | 2010/0074221 | 7/2010 |
| KR | 2012/0123055 | 11/2012 |

(56) References Cited

FOREIGN PATENT DOCUMENTS

| | | |
|---|---|---|
| RU | 94028282 | 7/1996 |
| RU | 2232773 | 7/2004 |
| RU | 2266298 | 12/2005 |
| TW | 2007/22517 | 6/2007 |
| WO | WO 89/01343 | 2/1989 |
| WO | WO 91/01335 | 2/1991 |
| WO | WO 92/19759 | 11/1992 |
| WO | WO 94/05690 | 3/1994 |
| WO | WO 95/33844 | 12/1995 |
| WO | WO 96/11020 | 4/1996 |
| WO | WO 96/12503 | 5/1996 |
| WO | WO 96/27011 | 9/1996 |
| WO | WO 97/09351 | 3/1997 |
| WO | WO 97/10354 | 3/1997 |
| WO | WO 98/03546 | 1/1998 |
| WO | WO 98/50431 | 11/1998 |
| WO | WO 99/18212 | 4/1999 |
| WO | WO 99/51743 | 10/1999 |
| WO | WO 99/58572 | 11/1999 |
| WO | WO 01/30854 | 5/2001 |
| WO | WO 01/82899 | 11/2001 |
| WO | WO 02/060919 | 8/2002 |
| WO | WO 02/072605 | 9/2002 |
| WO | WO 03/000883 | 1/2003 |
| WO | WO 03/020949 | 3/2003 |
| WO | WO 2004/016740 | 2/2004 |
| WO | WO 2004/020579 | 3/2004 |
| WO | WO 2004/068931 | 8/2004 |
| WO | WO 2004/096273 | 11/2004 |
| WO | WO 2004/113387 | 12/2004 |
| WO | WO 2005/005604 | 1/2005 |
| WO | WO 2005/035756 | 4/2005 |
| WO | WO 2005/047327 | 5/2005 |
| WO | WO 2005/056606 | 6/2005 |
| WO | WO 2005/059106 | 6/2005 |
| WO | WO 2005/062916 | 7/2005 |
| WO | WO 2005/067620 | 7/2005 |
| WO | WO 2005/092925 | 10/2005 |
| WO | WO 2005/112564 | 12/2005 |
| WO | WO 2005/123126 | 12/2005 |
| WO | WO 2006/004663 | 1/2006 |
| WO | WO 2006/019447 | 2/2006 |
| WO | WO 2006/029879 | 3/2006 |
| WO | WO 2006/030200 | 3/2006 |
| WO | WO 2006/030220 | 3/2006 |
| WO | WO 2006/033386 | 3/2006 |
| WO | WO 2006/047340 | 5/2006 |
| WO | WO 2006/047350 | 5/2006 |
| WO | WO 2006/050491 | 5/2006 |
| WO | WO 2006/065208 | 6/2006 |
| WO | WO 2006/067913 | 6/2006 |
| WO | WO 2006/071877 | 7/2006 |
| WO | WO 2006/075668 | 7/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/116260 | 11/2006 |
| WO | WO 2006/121852 | 11/2006 |
| WO | WO2007009065 * | 1/2007 |
| WO | WO 2007/024535 | 3/2007 |
| WO | WO 2007/060411 | 5/2007 |
| WO | WO 2007/108559 | 9/2007 |
| WO | WO 2007/114319 | 10/2007 |
| WO | WO 2007/114325 | 10/2007 |
| WO | WO 2008/090960 | 7/2008 |
| WO | WO 2008/092117 | 7/2008 |
| WO | WO 2008/119353 | 10/2008 |
| WO | WO 2008/145141 | 12/2008 |
| WO | WO 2008/145142 | 12/2008 |
| WO | WO 2009/036209 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/052439 | 4/2009 |
| WO | WO 2009/053368 | 4/2009 |
| WO | WO 2009/072604 | 6/2009 |
| WO | WO 2009/079649 | 6/2009 |
| WO | WO 2009/089004 | 7/2009 |
| WO | WO 2009/100309 | 8/2009 |
| WO | WO 2010/063746 | 6/2010 |
| WO | WO 2010/064090 | 6/2010 |
| WO | WO 2010/107109 | 9/2010 |
| WO | WO 2010/107110 | 9/2010 |
| WO | WO 2010/115589 | 10/2010 |
| WO | WO 2010/151792 | 12/2010 |
| WO | WO 2011/037158 | 3/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/108502 | 9/2011 |
| WO | WO 2011/111007 | 9/2011 |
| WO | WO 2011/125674 | 10/2011 |
| WO | WO 2011/131746 | 10/2011 |
| WO | WO 2011/133886 | 10/2011 |
| WO | WO 2011/143545 | 11/2011 |
| WO | WO 2012/020096 | 2/2012 |
| WO | WO 2012/067176 | 5/2012 |
| WO | WO 2012/145238 | 10/2012 |
| WO | WO 2013/060867 | 5/2013 |
| WO | WO 2013/124450 | 8/2013 |
| WO | WO 2013/136186 | 9/2013 |
| WO | WO 2013/157954 | 10/2013 |
| WO | WO 2014/028354 | 2/2014 |
| WO | WO 2014/054804 | 4/2014 |
| WO | WO 2014/067011 | 5/2014 |
| WO | WO 2015/046467 | 4/2015 |
| WO | WO 2015/063339 | 5/2015 |
| WO | WO 2016/159213 | 10/2016 |
| WO | WO 2017/115773 | 7/2017 |

OTHER PUBLICATIONS

Fish & Richardson P.C., Fourth Preliminary Amendment and Response to Restriction Requirement dated Jun. 6, 2012 in U.S. Appl. No. 12/680,082, filed Jun. 29, 2012, 13 pages.

USPTO Restriction Requirement in U.S. Appl. No. 12/680,082, dated Sep. 14, 2012, 6 pages.

Fish & Richardson P.C., Amendment and Response to Election Requirement dated Sep. 14, 2012 in U.S. Appl. No. 12/680,082, filed Nov. 8, 2012, 14 pages.

USPTO Non-Final Office Action U.S. Appl. No. 12/680,082, dated Feb. 14, 2013, 12 pages.

Hombach et al., "A CD16/CD30 bispecific monoclonal antibody induces lysis of Hodgkin's cells by unstimulated natural killer cells in vitro and in vivo," *Int J Cancer*, 55:830-6 (1993).

Paul, "Structure and function of immunoglobulins," Fundamental Immunology, Third Edition, 292-295 (1993).

Roguska et al., "Humanization of murine monoclonal antibodies through variable domain resurfacing," *Proc Natl Acad Sci U.S.A.*, 91:969-73 (1994).

Staerz et al., "Hybrid hybridoma producing a bispecific monoclonal antibody that can focus effector T-cell activity," *Proc Natl Acad Sci U.S.A.*, 83:1453-7 (1986).

Fish & Richardson P.C., Amendment in Reply to Office Action dated Jul. 2, 2013 in U.S. Appl. No. 13/257,145, filed Dec. 2, 2013, 12 pages.

USPTO Final Office Action in U.S. Appl. No. 13/257,145, dated Feb. 6, 2014, 12 pages.

Fish & Richardson P.C., Amendment and Response to Election Requirement dated Oct. 15, 2013 in U.S. Appl. No. 13/257,112, filed Nov. 15, 2013, 6 pages.

USPTO Non-Final Office Action in U.S. Appl. No. 13/257,112, dated Jan. 30, 2014, 18 pages.

Allen et al., "Interchain disulfide bonding in human IgG2 antibodies probed by site-directed mutagenesis," *Biochemistry*, 48(17):3755-66 (2009).

(56) References Cited

OTHER PUBLICATIONS

Fish & Richardson P.C., Response to Restriction Requirement dated Dec. 6, 2012 in U.S. Appl. No. 13/497,269, filed May 1, 2013, 2 pages.
Fish & Richardson P.C., Preliminary Amendment and Response to Restriction Requirement dated Mar. 20, 2013 in U.S. Appl. No. 13/257,145, filed Apr. 22, 2013, 7 pages.
Manz et al., Bioanalytical Chemistry, World Scientific Publishing Co. (2003).
Smans et al., "Bispecific antibody-mediated lysis of primary cultures of ovarian carcinoma cells using multiple target antigens," *Int. J. Cancer*, 83:270-277 (1999).
USPTO Non-Final Office Action in U.S. Appl. No. 12/295,075, dated Jun. 7, 2013, 17 pages.
Fish & Richardson P.C., Amendment in Reply to Action dated Jan. 3, 2013 in U.S. Appl. No. 12/679,922, filed Jul. 2, 2013, 18 pages.
USPTO Non-Final Office Action in U.S. Appl. No. 13/257,145, dated Jul. 2, 2013, 20 pages.
Baker et al., "Conversion of a T cell antagonist into an agonist by repairing a defect in the TCR/peptide/MHC interface: implications for TCR signaling," *Immunity*, 13:475-484 (2000).
Bowie et al., "Deciphering the message in protein sequences: tolerance to amino acid substitutions," *Science*, 247:1306-1310 (1990).
Burgess, "Possible dissociation of the heparin-binding and mitogenic activities of heparin-binding (acidic fibroblast) growth factor-1 from its receptor-binding activities by site-directed mutagenesis of a single lysine residue," *J. Cell. Biol.*, 111:2129-2138 (1990).
Ju et al., "Conversion of the interleukin 1 receptor antagonist into an agonist by site-specific mutagenesis," *Proc. Natl. Acad. Sci. U.S.A.*, 88:2658-2662 (1991).
Lazar et al., "Transforming growth factor alpha: mutation of aspartic acid 47 and leucine 48 results in different biological activities," *Mol. Cell Biol.*, 8:1247-1252 (1988).
Pakula et al., "Genetic Analysis of Protein Stability and Function," *Annu. Rev. Genet.*, 23:289-310 (1989).
Roitt et al., Immunology, M., Mir, (2000), pp. 110-111 (in Russian, with what is believed to be a published English equivalent of those pp. taken from Roitt et al., "Antibody Structure and Function," Immunology, Fifth Ed., (1998), pp. 80-81).
Shields et al., "High resolution mapping of the binding site on human IgG1 for Fc gamma RI, Fc gamma RIi, Fc gamma RIII, and FcRn and design of IgG1 variants with improved binding to the Fc gamma R," *J. Biol. Chem.*, 276(9):6591-604 (2001) (Epub Nov. 28, 2000).
USPTO Final Office Action in U.S. Appl. No. 12/679,922, dated Aug. 2, 2013, 12 pages.
USPTO Non-Final Office Action in U.S. Appl. No. 13/497,269, dated Aug. 15, 2013, 13 pages.
Fish & Richardson P.C., Amendment in Reply to Non-Final Office Action dated Feb. 14, 2013 in U.S. Appl. No. 12/680,082, filed Aug. 12, 2013, 17 pages.
Aslan et al., "Engineering a novel, stable dimeric streptavidin with lower isoelectric point," *J. Biotechnol.*, 128(2):213-25 (2007).
Atwell et al., "Stable heterodimers from remodeling the domain interface of a homodimer using a phage display library," *J. Mol. Biol.*, 270:26-35 (1997).
Baerga-Ortiz et al., "Two different proteins that compete for binding to thrombin have opposite kinetic and thermodynamic profiles," *Protein Sci.*, 13(1):166-76 (2004).
Carter, "Bispecific human IgG by design," *J. Immunol. Methods*, 248:7-15 (2001).
Dumont et al., "Monomeric Fc fusions: impact on pharmacokinetic and biological activity of protein therapeutics," *BioDrugs.*, 20(3):151-60 (2006).
Jendeberg et al., "Engineering of Fc(1) and Fc(3) from human immunoglobulin G to analyse subclass specificity for staphylococcal protein A," *J. Immunol. Methods.*, 201(1):25-34 (1997).

Marti et al., "Inverse electrostatic effect: electrostatic repulsion in the unfolded state stabilizes a leucine zipper," *Biochemistry*, 43(39):12436-47 (2004).
Marvin et al., "Redesigning an antibody fragment for faster association with its antigen," Biochemistry, 42:7077-83 (2003).
Ridgway et al., "'Knobs-into-holes' engineering of antibody $C_H3$ domains for heavy chain heterodimerization," *Protein Eng.*, 9:617-621 (1996).
Van Loghem et al., "Staphylococcal protein A and human IgG subclasses and allotypes," *Scand. J. Immunol.*, 15(3):275-8 (1982).
USPTO Final Office Action U.S. Appl. No. 12/680,082, dated Oct. 22, 2013, 12 pages.
USPTO Restriction Requirement in U.S. Appl. No. 11/910,128, dated Jun. 9, 2011, 10 pages.
Fish & Richardson P.C., Response to Restriction Requirement dated Jun. 9, 2011 in U.S. Appl. No. 11/910,128, filed Dec. 2, 2011, 1 page.
USPTO Non-Final Office Action in U.S. Appl. No. 11/910,128, dated Apr. 25, 2012, 21 pages.
Fish & Richardson P.C., Amendment in Reply to Office Action dated Apr. 25, 2012 in U.S. Appl. No. 11/910,128, filed Oct. 25, 2012, 32 pages.
Fish & Richardson P.C., Supplemental Amendment in U.S. Appl. No. 11/910,128, filed Nov. 14, 2012, 20 pages.
USPTO Final Office Action in U.S. Appl. No. 11/910,128, dated Sep. 10, 2013, 12 pages.
USPTO Restriction Requirement in U.S. Appl. No. 13/257,112, dated Oct. 15, 2013, 10 pages.
Fish & Richardson P.C., Amendment in Reply to Office Action dated Feb. 6, 2014 in U.S. Appl. No. 13/257,145, filed May 6, 2014, 10 pages.
U.S. Appl. No. 12/679,922, Igawa et al., filed Oct. 1, 2010.
U.S. Appl. No. 13/257,112, Igawa et al., filed Nov. 22, 2011.
Datta-Mannan et al., "Monoclonal antibody clearance. Impact of modulating the interaction of IgG with the neonatal Fc receptor," *J Biol Chem.*, 282(3):1709-17 (2007).
Jackman et al., "Development of a two-part strategy to identify a therapeutic human bispecific antibody that inhibits IgE receptor signaling," *J Biol Chem.*, Jul. 2, 2010;285(27): 20850-9. doi: 10.1074/jbc.M110.113910. Epub May 5, 2010.
Lin et al., "Preclinical pharmacokinetics, interspecies scaling, and tissue distribution of a humanized monoclonal antibody against vascular endothelial growth factor," *J Pharmacol Exp Ther.*, 288(1):371-8 (1999).
Spiess et al., "Bispecific antibodies with natural architecture produced by co-culture of bacteria expressing two distinct half-antibodies," *Nat Biotechnol.*, Aug. 2013; 31(8):753-8. doi: 10.1038/nbt.2621. Epub Jul. 7, 2013.
USPTO Final Office Action in U.S. Appl. No. 13/257,112, dated Sep. 5, 2014, 16 pages.
USPTO Notice of Allowance in U.S. Appl. No. 13/257,145, dated Oct. 1, 2014, 9 pages.
Jain et al., "Engineering antibodies for clinical applications," *Trends Biotechnol.*, 25(7):307-16 (2007).
Kufer et al., "A revival of bispecific antibodies," *Trends Biotechnol.*, 22(5):238-44 (2004).
Wally et al., "Identification of a novel substitution in the constant region of a gene coding for an amyloidogenic kappa1 light chain," *Biochim Biophys Acta.*, May 31, 1999;1454(1):49-56.
Abe et al., "Purification of monoclonal antibodies with light-chain heterogeneity produced by mouse hybridomas raised with NS-1 myelomas: application of hydrophobic interaction high-performance liquid chromatography," *J. Biochem. Biophys. Methods*, 27:215-227 (1993).
Adams et al "Humanization of a recombinant monoclonal antibody to produce a therapeutic HER dimerization inhibitor, pertuzumab," *Cancer Immunol. Immunother.*, 55:717-727 (2006).
Amersham Biosciences, "Affinity Chromatography: Principles and Methods," Edition AD, pp. 16-18, 137 (2002).
Amersham Biosciences, "Protein Purification Handbook, " Edition AC, 98 pages (2001).

(56) References Cited

OTHER PUBLICATIONS

Armour et al., "Recombinant human IgG molecules lacking Fcgamma receptor I binding and monocyte triggering activities," *Eur. J. Immunol.*, 29(8):2613-24 (1999).
Bartelds et al., "Clinical response to adalimumab: relationship to anti-adalimumab antibodies and serum adalimumab concentrations in rheumatoid arthritis," *Ann Rheum. Dis.*, 66:921-926 (2007).
Bender et al "Immunogenicity, efficacy and adverse events of adalimumab in RA patients," *Rheumatol. Int.*, 27:269-274 (2007).
Binz et al., "Engineering novel binding proteins from nonimmunoglobulin domains," *Nat. Biotechnol.*, 23:1257-68 (2005).
Brown et al., "Tolerance of single, but not multiple, amino acid replacements in antibody $V_H$CDR 2: a means of minimizing B cell wastage from somatic hypermutation?," *J. Immunol.*, 156(9):3285-91 (1996).
Chau et al., "HuM291(Nuvion), a humanized Fc receptor-nonbinding antibody against CD3, anergizes peripheral blood T cells as partial agonist of the T cell receptor," *Transplantation.*, 71(7):941-50 (2001).
Chirino et al., "Minimizing the immunogenicity of protein therapeutics," *Drug Discov. Today.*, 9:82-90 (2004).
Cole et al., "Human IgG2 variants of chimeric anti-CD3 are nonmitogenic to T cells," *J. Immunol.*, 159(7):3613-21 (1997).
Cordoba et al., "Non-enzymatic hinge region fragmentation of antibodies in solution," *J. Chromatogr. B. Analyt. Technol. Biomed. Life Sci.*, 818(2):115-21 (2005).
Couto et al., "Anti-BA46 Monoclonal Antibody Mc3: Humanization Using a Novel Positional Consensus and in Vivo and in Vitro Characterization," *Cancer Res.*, 55:1717-22 (1995).
Dall'Acqua et al., "Antibody humanization by framework shuffling," *Methods*, 36(1):43-60 (2005).
Dall'Acqua et al., "Modulation of the effector functions of a human IgG1 through engineering of its hinge region," *J. Immunol.*, 177(2):1129-38 (2006).
Deng et al., "An Agonist Murine Monoclonal Antibody to the Human c-Mpl Receptor Stimulates Megakaryocytopoiesis," *Blood*, 92:1981-88 (1998).
Dillon et al., "Structural and functional characterization of disulfide isoforms of the human IgG2 subclass," *J. Biol. Chem.*, 283(23):16206-15 (2008).
Ewert et al., "Stability improvement of antibodies for extracellular and intracellular applications: CDR grafting to stable frameworks and structure-based framework engineering," *Methods*, 34:184-199 (2004).
Gessner et al., "The IgG Fc receptor family," *Ann Hematol.*, 76(6):231-48 (1998).
Ghetie et al., "Increasing the serum persistence of an IgG fragment by random mutagenesis," *Nat. Biotechnol.*, 15:637-640 (1997).
Ghetie et al., "FcRn: the MHC class I-related receptor that is more than an IgG transporter," *Immunol. Today*, 18:592-598 (1997).
Gobburu et al., "Pharmacokinetics/dynamics of 5c8, a monoclonal antibody to CD154 (CD40 ligand) suppression of an immune response in monkeys," *J. Pharmacol. Exp. Ther.*, 286:925-930 (1998).
Graves et al., "Molecular modeling and preclinical evaluation of the humanized NR-LU-13 antibody," *Clin. Cancer Res.*, 5:899-908 (1999).
Guyre et al., "Increased potency of Fc-receptor-targeted antigens," *Cancer Immunol. Immunother.*, 45(3-4):146-8 (1997).
He et al., "Humanization and pharmacokinetics of a monoclonal antibody with specificity for both E- and P-selectin," *J. Immunol.*, 160:1029-35 (1998).
Hinton et al., "An engineered human IgG1 antibody with longer serum half-life," *J. Immunol.*, 176:346-356 (2006).
Hwang et al., "Use of human germline genes in a CDR homology-based approach to antibody humanization," *Methods*, 36:35-42 (2005).
Jefferis et al., "Recognition sites on human IgG for Fc gamma receptors: the role of glycosylation," *Immunol. Lett.*, 44(2-3):111-7 (1995).

Johnson et al., "Cation exchange-HPLC and mass spectrometry reveal C-terminal amidation of an IgG1 heavy chain," *Anal. Biochem.*, 360(1):75-83 (2007).
Jones et al., "Identification and removal of a promiscuous CD4+ T cell epitope from the C1 domain of factor VIII," *Thromb. Haemost.*, 3:991-1000 (2005).
Kashmiri et al., "Generation, characterization, and in vivo studies of humanized anticarcinoma antibody CC49," *Hybridoma*, 14:461-473 (1995).
Kim et al., "Antibody Engineering for the Development of Therapeutic Antibodies," *Mol. Cells*, 20:17-29 (2005).
Kranenborg et al., "Development and characterization of anti-renal cell carcinoma x antichelate bispecific monoclonal antibodies for two-phase targeting of renal cell carcinoma," *Cancer Res.*, 55:5864s-5867s (1995).
Lansdorp et al., "Purification and analysis of bispecific tetrameric antibody complexes," *Mol. Immunol.*, 27:659-666 (1990).
Lobo et al., "Antibody pharmacokinetics and pharmacodynamics," *J. Pharm. Sci.*, 93:2645-68 (2004).
MacCallum et al., "Antibody-antigen interactions: contact analysis and binding site topography," *J. Mol. Biol.*, 262:732-45 (1996).
Maini et al., "Double-blind randomized controlled clinical trial of the interleukin-6 receptor antagonist, tocilizumab, in European patients with rheumatoid arthritis who had an incomplete response to methotrexate," *Arthritis Rheum.*, 54:2817-29 (2006).
Morimoto et al., "Single-step purification of F(ab')2 fragments of mouse monoclonal antibodies (immunoglobulins G1) by hydrophobic interaction high performance liquid chromatography using TSKgel Phenyl-5PW," *J. Biochem. Biophys. Methods*, 24:107-117 (1992).
Nishimoto et al., "Interleukin 6: from bench to bedside," *Nat. Clin. Pract. Rheumatol.*, 2:619-626 (2006).
Nishimoto et al., "Humanized anti-interleukin-6 receptor antibody treatment of multicentric Castleman disease," *Blood*, 106:2627-32 (2005).
Onda et al., "Lowering the Isoelectric Point of the Fv Portion of Recombinant Immunotoxins Leads to Decreased Nonspecific Animal Toxicity without Affecting Antitumor Activity," *Cancer Res.*, 61:5070-77 (2001).
Pavlou et al., "The therapeutic antibodies market to 2008," *Eur. J. Pharm. Biopharm.*, 59(3):389-96 (2005).
Poduslo et al., "Polyamine modification increases the permeability of proteins at the blood—nerve and blood-brain barriers," *J. Neurochem.*, 66:1599-1609 (1996).
Presta et al., "Molecular engineering and design of therapeutic antibodies," *Curr. Opin. Immunol.*, 20(4).460-70. doi: 10.1016/j.coi.2008.06.012 (2008).
Rajpal et al., A general method for greatly improving the affinity of antibodies by using combinatorial libraries, Proc. Natl. Acad. Sci. USA, 102:8466-71 (2005).
Reddy et al., "Elimination of Fc receptor-dependent effector functions of a modified IgG4 monoclonal antibody to human CD4," *J. Immunol.*, 164(4):1925-33 (2000).
Reichert et al., "Monoclonal antibody successes in the clinic," *Nat. Biotechnol.*, 23(9):1073-8 (2005).
Rothe et al., "Ribosome display for improved biotherapeutic molecules," *Expert Opin. Biol. Ther.*, 6:177-187 (2006).
Salfeld et al., "Isotype selection in antibody engineering," *Nat. Biotechnol.*, 25:1369-72 (2007).
Sarmay et al., "Mapping and comparison of the interaction sites on the Fc region of IgG responsible for triggering antibody dependent cellular cytotoxicity (ADCC) through different types of human Fc gamma receptor," *Mol. Immunol.*, 29(5):633-9 (1992).
Sato et al., "Reshaping a human antibody to inhibit the interleukin 6-dependent tumor cell growth," *Cancer Res.*, 53:851-856 (1993).
Shire et al., "Challenges in the development of high protein concentration formulations," *J. Pharm. Sci.*, 93(6):1390-402 (2004).
Strand et al., "Biologic therapies in rheumatology: lessons learned, future directions," *Nat. Rev. Drug Discov.*, 6(1):75-92 (2007).
Sun et al., "Coexpression of Gas6/Axl in human ovarian cancers," *Oncology*, 66(6):450-7 (2004).
Suresh et al., "Bispecific monoclonal antibodies from hybrid hybridomas," Methods Enzymol., 121:210-228 (1986).

(56) References Cited

OTHER PUBLICATIONS

Tsurushita et al., "Design of humanized antibodies: From anti-Tac to Zenapax," *Methods*, 36:69-83 (2005).
Warnaar et al., "Purification of bispecific F(ab')2 from murine trinoma OC/TR with specificity for CD3 and ovarian cancer," *Hybridoma*, 13:519-526 (1994).
Wu et al., "Development of motavizumab, an ultra-potent antibody for the prevention of respiratory syncytial virus infection in the upper and lower respiratory tract," *J Mol. Biol.*, 368:652-665 (2007).
Xiang et al., "Study of B72.3 combining sites by molecular modeling and site-directed mutagenesis," *Protein Eng.*, 13(5):339-44 (2000).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," *J. Pharmacol. Exp. Ther.*, 301:467-477 (2002).
Zhu et al., "MHC class I-related neonatal Fc receptor for IgG is functionally expressed in monocytes, intestinal macrophages, and dendritic cells," *J. Immunol.*, 166(5):3266-76 (2001).
Zuckier et al., "Chimeric human-mouse IgG antibodies with shuffled constant region exons demonstrate that multiple domains contribute to in vivo half-life," Cancer Res., 58:3905-08 (1998).
International Search Report for Appl. Ser. No. PCT/JP2011/055101, dated May 10, 2011, 4 pages.
International Preliminary Report on Patentability for App. Ser. No. PCT/JP2011/055101, dated Oct. 2, 2012, 6 pages.
International Search Report App. Ser. No. PCT/JP2007/057058, dated May 7, 2001, 2 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed Dec. 27, 2011, 14 pages.
USPTO Final Office Action in U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed Sep. 11, 2012, 12 pages.
USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed Nov. 1, 2012, 2 pages.
USPTO Non-Final Office Action in U.S. Appl. No. 12/679,922, dated Jan. 3, 2013, 25 pages.
USPTO Restriction Requirement in U.S. Appl. No. 12/936,587, dated Dec. 6, 2011, 7 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed Jul. 25, 2012, 1 page.
USPTO Non-Final Office Action in U.S. Appl. No. 12/936,587, dated Nov. 7, 2012, 13 pages.
USPTO Non-Final Office Action in U.S. Appl. No. 13/595,139, dated Nov. 14, 2012, 10 pages.
USPTO Restriction Requirement in U.S. Appl. No. 13/497,269, dated Dec. 6, 2012, 9 pages.
USPTO Restriction Requirement in U.S. Appl. No. 12/295,075, dated Feb. 22, 2011, 9 pages.
Fish & Richardson P.C., Response to Restriction Requirement dated Feb. 22, 2011 in U.S. Appl. No. 12/295,075, filed Aug. 18, 2011, 2 pages.
USPTO Non-Final Office Action in U.S. Appl. No. 12/295,075, dated Nov. 4, 2011, 14 pages.
Fish & Richardson P.C., Amendment in Reply to Action dated Nov. 4, 2011 in U.S. Appl. No. 12/295,075, filed May 3, 2012, 12 pages.
USPTO Final Office Action in U.S. Appl. No. 12/295,075, dated Jul. 19, 2012, 12 pages.
Fish & Richardson P.C., Amendment in Reply to Action dated Jul. 19, 2012 in U.S. Appl. No. 12/295,075, filed Jan. 17, 2013, 113 pages.
Tsubaki et al., "C-terminal modification of monoclonal antibody drugs: amidated species as a general product-related substance," *Int J Biol Macromol.*, 52:139-47. doi: 10.1016/j.ijbiomac.2012.09.016. Epub Sep. 25, 2012.
Fish & Richardson P.C., Amendment and Reply to Non-Final Office Action dated Jan. 30, 2014 in U.S. Appl. No. 13/257,112, filed Jul. 1, 2014, 12 pages.
Queen et al., "A humanized antibody that binds to the interleukin 2 receptor," *Proc. Natl. Acad. Sci. USA.*, 86(24):10029-10033 (1989).
USPTO Restriction Requirement in U.S. Appl. No. 13/257,145, dated Mar. 20, 2013, 11 pages.
Fish & Richardson P.C., Amendment and Reply to Final Office Action dated Sep. 5, 2014 in U.S. Appl. No. 13/257,112, filed Feb. 5, 2015, 6 pages.
Bowie et al., "Deciphering the Message in Protein Sequences: Tolerance to Amino Acid Substitutions," *Science*, Mar. 16, 1990;247:1306-1310.
Medesan et al., "Delineation of the amino acid residues involved in transcytosis and catabolism of mouse IgG1,"*J Immunol.*, Mar. 1, 1997;158(5):2211-7.
Pan et al., "Blocking neuropilin-1 function has an additive effect with anti-VEGF to inhibit tumor growth," *Cancer Cell*, Jan. 2007;11(1):53-67.
Singer et al., Genes & Genomes, 1991;67-69.
Singer et al., Genes & Genomes, 1998;1:63-64.
USPTO Notice of Allowance in U.S. Appl. No. 13/257,112, dated Feb. 23, 2015, 8 pages.
USPTO Notice of Allowance in U.S. Appl. No. 13/257,112, dated Apr. 2, 2015, 7 pages.
McPhee et al., "Engineering human immunodeficiency virus 1 protease heterodimers as macromolecular inhibitors of viral maturation," *Proc Natl Acad Sci U S A.*, Oct. 15, 1996;15;93(21):11477-81.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," *Biochemistry*, Jun. 30, 1987;26(13):4131-8.
Johnson et al., "Kabat database and its applications: 30 years after the first variability plot," *Nucleic Acids Res.*, Jan. 1, 2000;28(1):214-8.
USPTO Notice of Allowance in U.S. Appl. No. 13/257,145, dated Jan. 9, 2015, 7 pages.
USPTO Notice of Allowance in U.S. Appl. No. 13/257,145, dated Mar. 11, 2015, 7 pages.
U.S. Appl. No. 14/962,293, Igawa et al.
Algonomics—Tripole® applications [online] Retrieved from the Internet on Feb. 29, 2012: http://web.archive.org/web20090221052902/ http://www.algonomics.com/proteinengineering/tripole_applications. php, 2 pages (Feb. 21, 2009).
Allard et al., "Antigen binding properties of highly purified bispecific antibodies," Mol Immunol., Oct. 1992;29(10):1219-27.
Almagro et al., "Humanization of antibodies," Front Biosci., Jan. 1, 2008;13:1619-33.
Arndt et al., "Factors influencing the dimer to monomer transition of an antibody single-chain Fv fragment," Biochemistry, 37(37):12918-26 (1998).
Batra et al., "Pharmacokinetics and biodistribution of genetically engineered antibodies," Curr Opin Biotechnol., Dec. 2002;13(6):603-8.

(56) References Cited

OTHER PUBLICATIONS

Bian et al., "Discovery of promiscuous HLA-II-restricted T cell epitopes with TELPITOPE," Methods, Dec. 2004;34(4):468-75.
Branden et al., "Recognition of Foreign Molecules by the Immune System," Introduction to Protein Structure, 2d Ed., Garland Publishing, pp. 299-323 (1999).
Burges et al., "Effective relief of malignant ascites in patients with advanced ovarian cancer by a trifunctional anti-EpCAM x anti-CD3 antibody: a phase I/II study," Clin Cancer Res., Jul. 1, 2007;13(13):3899-905.
CALBIOCHEM® Buffers, "A guide for the preparation and use of buffers in biological systems," by Chandra Mohan, Ph.D., Copyright © 2003 EMD Biosciences, Inc., an Affiliate of Merck KGaA, Darmstadt, Germany, 37 pages.
Chamow et al., "A humanized, bispecific immunoadhesin-antibody that retargets CD3+ effectors to kill HIV-1-infected cells," J. Immunol., 153(9):4268-80 (1994).
Chappel et al., "Identification of a secondary Fc gamma RI binding site within a genetically engineered human IgG antibody," J Biol Chem., Nov. 25, 1993;268(33):25124-31.
Chappel et al., "Identification of the Fc gamma receptor class I binding site in human IgG through the use of recombinant IgG1/IgG2 hybrid and point-mutated antibodies," Proc Natl Acad Sci U S A., Oct. 15, 1991;88(20):9036-40.
Chatellier et al., "Functional mapping of conserved residues located at the VL and VH domain interface of a Fab," *J. Mol. Biol.*, Nov. 22, 1996;264(1):1-6.
Chen et al., "Generation and analysis of random point mutations in an antibody CDR2 sequence: many mutated antibodies lose their ability to bind antigen," J Exp Med., Sep. 1, 1992;176(3):855-66.
Chen et al., "Defective secretion of an immunoglobulin caused by mutations in the heavy chain complementarity determining region 2," J Exp Med., Aug. 1, 1994;180(2):577-86.
Chu et al., "Accumulation of succinimide in a recombinant monoclonal antibody in mildly acidic buffers under elevated temperatures," Pharm Res., Jun. 2007;24(6):1145-56. Epub Mar. 24, 2007.
Comper et al., "Charge selectivity in kidney ultrafiltration," Kidney Int., May. 1995;47(5):1242-51.
Damschroder et al., "Framework shuffling of antibodies to reduce immunogenicity and manipulate functional and biophysical properties," Mol. Immunol., Apr. 2007;44(11):3049-60. Epub Jan. 22, 2007.
Davies et al., "Antibody VH domains as small recognition units," Biotechnology (N.Y.), May 1995;13(5):475-9.
De Groot et al., "De-immunization of therapeutic proteins by T-cell epitope modification," Dev Biol. (Basel), 2005;122:171-94.
Deen et al., "Structural determinants of glomerular permeability," Am J Physiol Renal Physiol., Oct. 2001;281(4):F579-96.
Del Rio et al., "An Engineered Penicillin Acylase with Altered Surface Charge Is More Stable in Alkaline pH," Ann N Y Acad Sci., Oct. 12, 1996;799:61-4.
Dhiman et al., "Gene expression microarrays: a 21st century tool for directed vaccine design," Vaccine, Oct. 12, 2001;20(1-2):22-30.
Elliott et al., "Activation of the erythropoietin (EPO) receptor by bivalent anti-EPO receptor antibodies," J Biol Chem., Oct. 4, 1996;271(40):24691-7.
Fujii, "Antibody affinity maturation by random mutagenesis," Methods Mo. Biol., 2004;248:345-59.
Gerstner et al., "Sequence plasticity in the antigen-binding site of a therapeutic anti-HER2 antibody," J Mol Biol., Aug. 30, 2002;321(5):851-62.
Ghetie et al., "Multiple roles for the major histocompatibility complex class I—related receptor FcRn," Annu Rev Immunol., 2000;18:739-66.
Goode et al., "The glomerular basement membrane charge-selectivity barrier: an oversimplified concept?" Nephrol Dial Transplant., Sep. 1996;11(9):1714-6.
Greenwood et al., "Structural motifs involved in human IgG antibody effector functions," Eur J Immunol., May 1993;23(5):1098-104.

Griffin et al., "Analysis of heavy and light chain sequences of conventional camelid antibodies from *Camelus dromedarius* and *Camelus bactrianus* species," J Immunol Methods, Mar. 2014;405:35-46. doi: 10.1016/j.jim.2014.01.003. Epub Jan. 18, 2014.
Gunasekaran et al., "Enhancing antibody Fc heterodimer formation through electrostatic steering effects: applications to bispecific molecules and monovalent IgG," J. Biol. Chem., Jun. 18, 2010;285(25):19637-46. doi: 10.1074/jbc.M110.117382. Epub Apr. 16, 2010.
Gupta et al., "Affinity chromatography and co-chromatography of bispecific monoclonal antibody immunoconjugates," J. Biochem. Biophys. Methods, 51:203-216 (2002).
Haagen et al., "Unprimed CD4+ and CD8+ T cells can be rapidly activated by a CD3xCD19 bispecific antibody to proliferate and become cytotoxic," Cancer Immunol Immunother., Dec. 1994;39(6):391-6.
Hamers-Casterman et al., "Naturally occurring antibodies devoid of light chains," Nature, Jun. 3, 1993;363(6428):446-8.
Hinton et al., "Engineered human IgG antibodies with longer serum half-lives in primates," J Biol Chem., Feb. 20, 2004;279(8):6213-6. Epub Dec. 29, 2003.
Igawa et al., "VH/VL interface engineering to promote selective expression and inhibit conformational isomerization of thrombopoietin receptor agonist single-chain diabody," Protein Eng Des Sel., Aug. 2010;23(8):667-77. doi: 10.1093/protein/gzq034. Epub Jun. 24, 2010.
IMGT Scientific charts depicting the correspondence between Eu and Kabat numberings for the human IgG constant region, created May 17, 2001 and last updated Aug. 13, 2014.
Jung et al., "The importance of framework residues H6, H7 and H10 in antibody heavy chains: experimental evidence for a new structural subclassification of antibody V(H) domains," J. Mol. Biol., Jun. 8, 2001;309(3):701-16.
Kabat et al., Sequence of Proteins of Immunological Interest, $5^{th}$ Edition 1991, p. 690 and p. 693.
Kai et al., "Switching constant domains enhances agonist activities of antibodies to a thrombopoietin receptor," Nat Biotechnol., Feb. 2008;26(2):209-11. Epub Dec. 23, 2007.
Katayose et al., "MUC1-specific targeting immunotherapy with bispecific antibodies: inhibition of xenografted human bile duct carcinoma growth," Cancer Res., Sep. 15, 1996;56(18):4205-12.
Kenanova et al., "Tailoring the pharmacokinetics and positron emission tomography imaging properties of anti-carcinoembryonic antigen single-chain Fv-Fc antibody fragments," Cancer Res., Jan. 15, 2005;65(2):622-31.
Khalifa et al., "Effects on interaction kinetics of mutations at the VH-VL interface of Fabs depend on the structural context," J. Mol. Recognit., May-Jun. 2000;13(3):127-39.
Khawli et al., "Improved tumor localization and radioimaging with chemically modified monoclonal antibodies," Cancer Biother Radiopharm., Jun. 1996;11(3):203-15.
Kim et al., "Mapping the site on human IgG for binding of the Mhc class I-related receptor, FcRn," Eur. J. Immunol., Sep. 1999;29(9):2819-25.
Kim et al., "Chemical modification to reduce renal uptake of disulfide-bonded variable region fragment of anti-tac monoclonal antibody labeled with $^{99m}TC$," Bioconjug Chem., May-Jun. 1999;10(3):447-53.
Kim et al., "Lowering of pI by acylation improves the renal uptake of 99mTc-labeled anti-Tac dsFv: effect of different acylating reagents," Nucl Med Biol., Nov. 2002;29(8):795-801.
Kipriyanov et al., "Bispecific tandem diabody for tumor therapy with imprived antigen binding and pharmacokinetics," J Mol Biol., Oct. 15, 1999;293(1):41-56.
Kipriyanov et al., "Effect of Domain Order on the Activity of Bacterially Produced Bispecific Single-chain Fv Antibodies," J. Mol. Biol., Jun. 27, 2003;330(1):99-111.
Kobayashi et al., "The pharmacokinetic characteristics of glycolated humanized anti-Tac Fabs are determined by their isoelectric points," Cancer Res., Jan. 15, 1999;59(2):422-30.

(56) References Cited

OTHER PUBLICATIONS

Komissarov et al., "Site-specific mutagenesis of a recombinant anti-single-stranded DNA Fab. Role of heavy chain complementarity-determining region 3 residues in antigen interaction," J Biol Chem., Oct. 24, 1997;272(43):26864-70.
Koniermann, R., "Recombinant bispecific antibodies for cancer therapy," Acta Pharmacol Sin., Jan. 2005;26(1):1-9.
Korn et al., "Recombinant bispecific antibodies for the targeting of adenoviruses to CEA-expressing tumour cells: a comparative analysis of bacterially expressed single-chain diabody and tandem scFv," J Gene Med., Jun. 2004;6(6):642-651.
Kreutz et al., "Efficient bispecific monoclonal antibody purification using gradient thiophilic affinity chromatography," J. Chromatogr. B, 714:161-170 (1998).
Kumar et al., "The second PDZ domain of INAD is a type I domain involved in binding to eye protein kinase C. Mutational analysis and naturally occuring variants," J Biol Chem., Jul. 6, 2001;276(27):24971-7.
Kurfis et al., "Role of Arg182 in the second extracellular loop of angiotensin II receptor AT2 in ligand binding," Biochem Biophys Res Commun., Oct. 5, 1999;263:816-9.
Le Gall et al., "Effect of linker sequences between the antibody variable domains on the formation, stability and biological activity of a bispecific tandem diabody," Protein Eng Des Sel., Apr. 2004;17(4):357-66. Epub May 4, 2004.
Lebégue et al., "Production and characterization of hybrid monoclonal antibodies with IgG1/IgG3 double isotype," C R Acad Sci III., 1990;310(9):377-82.
Leong et al., "Adapting pharmacokinetic properties of a humanized anti-interleukin-8 antibody for therapeutic applications using site-specific pegylation," Cytokine, Nov. 7, 2001;16(3):106-19.
Lindhofer et al., "Preferential Species-Restricted Heavy/Light Chain Pairing in Rat/Mouse Quadromas," J. Immunol., 155:219-225 (1995).
Liu et al., "Functional interactions between arginine-133 and aspartate-88 in the human reduced folate carrier: evidence for a charge-pair association," Biochem J.,Sep. 1, 2001;358(Pt 2):511-6.
Liu et al., "Heterogeneity of monoclonal antibodies," J Pharm Sci., Jul. 2008;97(7):2426-47.
Lloyd et al., "The production of a bispecific anti-CEA, anti-hapten (4-amino-phthalate) hybrid-hybridoma," J Natl Med Assoc., Oct. 1991;83(10):901-4.
Lund et al., "Expression and characterization of truncated forms of humanized L243 IgG1. Architectural features can influence synthesis of its oligosaccharide chains and affect superoxide production triggered through human Fcgamma receptor I," Eur J Biochem., Dec. 2000;267(24):7246-56.
Maity et al., "Equilibrium unfolding of dimeric and engineered monomeric forms of Cro (F58W) repressor and the effect of added salts: evidence for the formation of folded monomer induced by sodium perchlorate," Arch Biochem Biophys., Feb. 1, 2005;434(1):93-107.
Male et al., "Antibodies"; Immunology, 7th Edition (2006), published by Elsevier Ltd., pp. 59-86.
Manzke et al., "Single-step purification of bispecific monoclonal antibodies for immunotherapeutic use by hydrophobic interaction chromatography," J. Immunol. Methods, 1997;208:65-73.
Martin et al., "Crystal structure at 2.8 A of an FcRn/heterodimeric Fc complex: mechanism of pH-dependent binding," Mol Cell., Apr. 2001;7(4):867-77.
Martinez et al., "Disulfide connectivity of human immunoglobulin G2 structural isoforms," Jul. 15, 2008;47(28):7496-508. doi: 10.1021/bi800576c. Epub Jun. 13, 2008.
Marvin et al., "Recombinant approaches to IgG-like bispecific antibodies," Acta Pharmacol Sin., Jun. 2005;26:649-58.
Merchant et al., "An efficient route to human bispecific IgG," Nat Biotechnol., Jul. 1998;16(7):677-81.
Michaelsen et al., "A mutant human IgG molecule with only one C1q binding site can activate complement and induce lysis of target cells," Eur J Immunol., Jan. 2006;36(1):129-38.

Morell et al., "Metabolic properties of IgG subclasses in man," J Clin Invest., Apr. 1970;49(4):673-80.
Narhi et al., "Asn to Lys mutations at three sites which are N-glycosylated in the mammalian protein decrease the aggregation of *Escherichia coli*-derived erythropoietin," Protein Eng., Feb. 2001;14(2):135-40.
Nesterova et al., "Glypican-3 as a novel target for an antibody-drug conjugate," AACR Abstract No. 656, Los Angeles, CA (Apr. 4-18, 2007).
Nieba et al., "Disrupting the hydrophobic patches at the antibody variable/constant domain interface: improved in vivo folding and physical characterization of an engineered scFv fragment," Protein Eng., Apr. 1997;10(4):435-44.
Nohaile et al., "Altering dimerization specificity by changes in surface electrostatics," Pro Natl Acad Sci U S A., Mar. 13, 2001;98(6):3109-14. Epub Feb. 27, 2001.
O'Shea et al., "Peptide 'Velcro': design of a heterodimeric coiled coil," Curr Biol., Oct. 1, 1993;3(10):658-67.
Ono et al., "The humanized anti-HM1.24 antibody effectively kills multiple myeloma cells by human effector cell-mediated cytotoxicity," Mol Immunol., Apr. 1999;36(6):387-95.
Ozhegov et al., Tolkovyi Slovar Russkogo iazyka: 2004, p. 292 (with an English translation of the relevant passage defining "control").
Pardridge et al., "Enhanced endocytosis in cultured human breast carcinoma cells and in vivo biodistribution in rats of a humanized monoclonal antibody after cationization of the protein," J Pharmacol Exp Ther., Jul. 1998; 286(1):548-54.
Pavlinkova et al., "Charge-modified single chain antibody constructs of monoclonal antibody CC49: Generation, characterization, pharmacokinetics, and biodistribution analysis," Nucl Med Biol., Jan. 1999;26(1):27-34.
Pokkuluri et al., "A domain flip as a result of a single amino-acid substitution," Structure, Aug. 15, 1998;6(8):1067-73.
Pons et al., "Energetic analysis of an antigen/antibody interface: alanine scanning mutagenesis and double mutant cycles on the HyHEL-10/lysozyme interaction," Protein Sci., May 1999;8(5):958-68.
Raffen et al., "Reengineering immunoglobulin domain interactions by introduction of charged residues," Protein Eng., Apr. 1998;11:303-9.
Reichert et al., "Development trends for monoclonal antibody cancer therapeutics," Nat Rev Drug Discov., May 2007; 6(5):349-56.
Reist et al., "Human IgG2 constant region enhances in vivo stability of anti-tenascin antibody 81C6 compared with its murine parent," Clin Cancer Res., Oct. 1998;4(10):2495-502.
Roitt et al., Immunology, M., Mir, 5th Edition (2000), pp. 97-113.
Rudikoff et al., "Single amino acid substitution altering antigen-binding specificity," Proc Natl Acad Sci. U.S.A., Mar. 1982;79(6):1979-83.
Ruf et al., "Pharmacokinetics and in vivo stability of intraperitoneally administered therapeutic antibody catumaxomab," J Clin Oncol., 26 (May 20 suppl) (2008), abstr 14006.
Sal-Man et al., "Arginine mutations within a transmembrane domain of Tar, an *Escherichia coli* aspartate receptor, can drive homodimer dissociation and heterodimer association in vivo," Biochem J., Jan. 1, 2005;385(Pt 1):29-36.
Schaeffer et al., "The Rat Glomerular Filtration Barrier Does Not Show Negative Charge Selectivity," Microcirculation, Oct. 2002;9(5):329-42.
Schmitz et al., "Phage display: a molecular tool for the generation of antibodies—a review," Placenta., Mar.-Apr. 2000;21 Suppl A:S106-12.
Segal et al., "Bispecific antibodies in cancer therapy," Curr Opin Immunol., Oct. 1999;11(5):558-62.
Shaul, "Exploring the charge space of protein-protein association: a proteomic study," Proteins, 60:341-352 (2005).
Sinha et al., "Electrostatics in protein binding and function," Curr Protein Pept Sci., Dec. 2002;3(6):601-14.
Smolen et al., "Interleukin-6: a new therapeutic target," Arthritis Res Ther., 2006;8 Suppl 2:S5. Epub Jul. 28, 2006.

(56) References Cited

OTHER PUBLICATIONS

Tan et al., "Contributions of a highly conserved $V_H/V_L$ hydrogen bonding interaction to scFv folding stability and refolding efficiency," Biophys J., Sep. 1998; 75(3):1473-82.
Tan et al., "Engineering the isoelectric point of a renal cell carcinoma targeting antibody greatly enhances scFv solubility," Immunotechnology, Oct. 1998;4(2):107-114.
Tarditi et al., "Selective high-performance liquid chromatographic purification of bispecific monoclonal antibodies," J. Chromatogr., 599:13-20 (1992).
Teeling et al., "The biological activity of human CD20 monoclonal antibodies is linked to unique epitopes on CD20," J Immunol., Jul. 1, 2006;177(1):362-71.
Ten Kate et al., "Effect of isoelectric point on biodistribution and inflammation. imaging with indium-111-labelled IgG," Eur. J. Nucl. Med., 1990;17(6-8):305-9 (abstract).
Thies et al., "The alternatively folded state of the antibody C(H)3 domain," J Mol Biol., Jun. 22, 2001;309(5):1077-85.
Vargas-Madrazo et al., "An improved model of association for VH-VL immunoglobulin domains. asymmetries between VH and VL in the packing of some interface residues," J Mol Recognit., May-Jun. 2003;16(3):113-20.
Vaisitti et al., "Cationization of monoclonal antibodies: another step towards the "magic bullet"?," J Biol Regul Homeost Agents., Jul.-Dec. 2005;19(3-4):105-12.
Vajdos et al., "Comprehensive functional maps of the antigen-binding site of an anti-EibB2 antibody obtained with shotgun scanning mutagenesis," J Mol Biol., Jul. 5, 2002;320(2):415-28.
Van Walle et al.,"Immunogenicity screening in protein drug development," Expert Opin Biol Ther., Mar. 2007;7(3):405-418.
Wang et al., "Conserved amino acid networks involved in antibody variable domain interactions," Proteins, Jul. 2009;76(1):99-114. doi: 10.1002/prot.22319.
Wang et al., "Polyethylene Glycol-modified Chimeric Toxin Composed of Transforming Growth Factor alpha and Pseudomonas Exotoxin," Cancer Res., Oct. 1, 1993;53:4588-94.
Wiens et al., "Somatic mutation in VH complementarity-determining region 2 and framework region 2: differential effects on antigen binding and Ig secretion," J Immunol., Aug. 1, 1997;159(3):1293-302.
Wiens et al., "Mutation of a single conserved residue in VH complementarity-determining region 2 results in a severe Ig secretion defect," J Immunol., Aug. 15, 2001;167(4):2179-86.
Worn et al., "Stability engineering of antibody single-chain Fv fragments," J Mol Biol., Feb. 2, 2001;305(5):989-1010.
Wu et al., "Multimerization of a chimeric anti-CD20 single-chain Fv-Fc fusion protein is mediated through variable domain exchange," Protein Eng., Dec. 2001;14(12):1025-33.
Wypych et al., "Human IgG2 antibodies display disulfide-mediated structural isoforms," J BiolChem., Jun. 6, 2008;283(23):16194-205. Epub Mar. 13, 2008.
Yang et al., "Tailoring structure-function and pharmacokinetic properties of single-chain Fv proteins by site-specific PEGylation," Protein Eng., Oct. 2003;16(10):761-70.
Zhu et al., "Remodeling domain interfaces to enhance heterodimer formation," Protein Sci., Apr. 1997;6(4):781-8.
Zwick et al., "The long third complementarity-determining region of the heavy chain is important in the activity of the broadly neutralizing anti-human immunodeficiency virus type 1 antibody 2F5," J Virol., Mar. 2004;78(6):3155-61.
USPTO Notice of Allowance in U.S. Appl. No. 13/257,112, dated Aug. 26, 2015, 7 pages.
Gramer et al., "Production of stable bispecific IgG1 by controlled Fab-arm exchange: scalability from bench to large-scale manufacturing by application of standard approaches," MAbs., Nov.-Dec. 2013;5(6):962-73. doi: 10.4161/mabs.26233. Epub Aug. 22, 2013.
Klein et al., "Progress in overcoming the chain association issue in bispecific heterodimeric IgG antibodies," MAbs., Nov.-Dec. 2012;4(6):653-63. doi: 10.4161/mabs.21379. Epub Aug. 27, 2012.

Labrijn et al., "Efficient generation of stable bispecific IgG1 by controlled Fab-arm exchange," Pro Natl Acad Sci U S A., Mar. 26, 2012;110(13):5145-50. doi: 10.1073/pnas.1220145110. Epub Mar. 11, 2013.
Labrijn et al., "Species-specific determinants in the IgG CH3 domain enable Fab-arm exchange by affecting the noncovalent CH3—CH3 interaction strength," J Immunol., Sep. 15, 2011;187(6):323-846. doi: 10.4049/jimmuno1.1003336. Epub Aug. 12, 2011.
Rispens et al., "Dynamics of inter-heavy chain interactions in human immunoglobulin G (IgG) subclasses studied by kinetic Fab arm exchange," J Biol Chem., Feb. 28, 2014;289(9):6098-109. doi: 10.1074/jbc.M113.541813. Epub Jan. 14, 2014.
Schaefer et al., "Immunoglobulin domain crossover as a generic approach for the production of bispecific IgG antibodies," Proc Natl Acad Sci U S A., Jul. 5, 2011;108(27):11187-92. doi: 10.1073/pnas.1019002108. Epub Jun. 20, 2011.
Schuurman et al., "Normal human immunoglobulin G4 is bispecific: it has two different antigen-combining sites," Immunology, Aug. 1999;97(4):693-8.
Schuurman et al., "The inter-heavy chain disulfide bonds of IgG4 are in equilibrium with intra-chain disulfide bonds," Mol Immunol., Jan. 2001;38(1):1-8.
Van Der Neut Kolfschoten et al., "Anti-inflammatory activity of human IgG4 antibodies by dynamic Fab arm exchange," Science, Sep. 14, 2007;317(5844):1554-7.
Brenner et al., "Errors in genome annotation," Trends in Genetics, Apr. 1999;15:132-133.
Chen et al., "Selection and analysis of an optimized anti-VEGF antibody: crystal structure of an affinity-matured Fab in complex with antigen," J Mol Biol., Nov. 5, 1999;293(4):865-81.
Choi et al., "Engineering of Immunoglobulin Fc Heterodimers Using Yeast Surface-Displayed Combinatorial Fc Library Screening," PLoS One, Dec. 16, 2015;10(12):e0145349. doi: 10.1371/journal.pone.0145349. eCollection 2015.
Coloma et al., "Position effects of variable region carbohydrate on the affinity and in vivo behavior of an anti-(1→6) dextran antibody," J Immunol., Feb. 15, 1999;162(4):2162-70.
Dall'Acqua et al., "Increasing the affinity of a human IgG1 for the neonatal Fc receptor: biological consequences," J. Immunol., Nov. 1, 2002;169(9):5171-80.
Hird et al., "Tumour localisation with a radioactively labelled reshaped human monoclonal antibody," Br J Cancer, Nov. 1991;64(5):911-4.
Hong et al., "Enhanced cellular uptake and transport of polyclonal immunoglobulin G and fab after their cationization," J Drug Target, 2000;8(2):67-77.
Ito et al., "The His-probe method: effects of histidine residues introduced into the complementarity-determining regions of antibodies on antigen-antibody interactions at different pH values," FEBS Lett., Aug. 31, 1992;309:85-8.
Li et al., "Construction and characterization of a humanized anti-human CD3 monoclonal antibody 12F6 with effective immunoregulation functions," Immunology, Dec. 2005;116(4):487-98.
Marshall et al., "Rational design and engineering of therapeutic proteins," Drug Discov Today, Mar. 1, 2003;8(5):212-21.
Pardridge et al., "Enhanced cellular uptake and in vivo biodistribution of a monoclonal antibody following cationization," J Pharm Sci., Aug. 1995;84(8):943-8.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Roopenian et al., "FcRn: the neonatal Fc receptor comes of age," Nat Rev Imnunol., Sep. 2007;7(9):715-25. Epub Aug. 17, 2007.
Sarkar et al., "Rational cytokine design for increased lifetime and enhanced potency using pH-activated histidine switching", Nat Biotechnol., Sep. 2002;20(9):908-13. Epub Aug. 5, 2002.
Sharifi et al., "Improving monoclonal antibody pharmacokinetics via chemical modification," Q J Nucl Med., Dec. 1998;42(4):242-9.
Smith et al., "The challenges of genome sequence annotation or 'the devil is in the details'," Nature Biotechnology, Nov. 1997;15:1222-1223.

(56) References Cited

OTHER PUBLICATIONS

Tabrizi et al., "Elimination mechanisms of therapeutic monoclonal antibodies," *Drug Discov Today*, Jan. 2006;11(1-2):81-8.
Verhoeyen et al., "Construction of a reshaped HMFG1 antibody and comparison of its fine specificity with that of the parent mouse antibody," *Immunology*, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Yang et al., "CDR walking mutagenesis for the affinity maturation of a potent human anti-HIV-1 antibody into the picomolar range," *J. Mol. Biol.*, Dec. 1, 1995;254(3):392-403.
Ejima et al., "Effects of Acid Exposure on the Conformation, Stability, and Aggregation of Monoclonal Antibodies," Proteins Mar. 1, 2007;66(4):954-62.
Gen Bank Accession No. AAG00910.2, "recombinant IgG2 heavy chain, partial [*Homo sapiens*]," May 14, 2001, 1 page.
Newman et al., "Modification of the Fc Region of a Primatized IgG Antibody to Human CD4 Retains Its Ability to Modulate CD4 Receptors but Does Not Deplete CD4 T Cells in Chimpanzees," Clin. Immunol. Feb. 2001;98(2):164-74.
U.S. Appl. No. 15/614,842, Igawa et al., filed Mar. 6, 2017.
Diaz et al., "Effects of engineering charged amino acids in the CH3 domains on antibody heavy chain dimerization," Philippine Science Letters. 2011;4(1):48-55.
Gunawardane et al., "Agonistic Human Antibodies Binding to Lecithin-Cholesterol Acyltransferase Modulate High Density Lipoprotein Metabolism," J Biol Chem. 2016 291:2799-811. doi: 10.1074/jbc.M115.672790.
Hattori, Introduction of ART-Ig and application to hemophilia A treatment, Chugai Seiyaku ni Okeru Dokuji no Kakushinteki Kotai Gijutsu. Dec. 2012; 18: 42-57
Janeway et al., Immunobiology, 5th edition. 2001: p. 93-122.
Janeway et al., Immunobiology, 5th edition. 2001: p. 123-154.
Kabat et al., Sequences of Proteins of Immunological Interest, Natl Inst Health, Pub. No. 91-3242, 1: 647-660 (1991).
Labrijn et al., "Controlled Fab-arm exchange for the generation of stable bispecific IgG1," Nat. Protoc. 2014 9: 2450-2463. doi: 10.1038/nprot.2014.169.
Murata et al., "Anti-Digoxin Fab Variants Generated by Phage Display," Mol Biotechnol. 2013 54: 269-277. doi:10.1007/s12033-012-9564-1.
Pejchal et al., "A Conformational Switch in Human Immunodeficiency Virus gp41 Revealed by the Structures of Overlapping Epitopes Recognized by Neutralizing Antibodies," J Virol. 2009 83: 8451-8462. doi : 10.1128/ JVI. 00685-09.
Peters et al., "Engineering an improved IgG4 molecule with reduced disulfide bond heterogeneity and increased Fab domain thermal stability," J Biol Chem. 2012 287: 24525-24533. doi: 10.1074/jbc.M112.369744.
Petkova et al., "Enhanced half-life of genetically engineered human IgG1 antibodies in a humanized FcRn mouse model: potential applicaton in humorally mediated autoimmune disease," Int Immunol. 2006 18: 1759-69.
Raposo et al., "Epitope-specific antibody response is controlled by immunoglobulin Vh polymorphisms," J Exp Med. 2014 211: 405-411. doi:10.1084/ jem.20130968.
Vaccaro et al., "Divergent activities of an engineered antibody in murine and human systems have implications for therapeutic antibodies," Proc Natl Acad Sci U S A. 2006 103: 18709-18714.
U.S. Appl. No. 15/875,847, Igawa et al., filed Jan. 19, 2018.
U.S. Appl. No. 16/061,454, Igawa et al., filed Jun. 12, 2018.
Canfield et al., "The Binding Affinity of Human IgG for its High Affinity Fc Receptor Is Determined by Multiple Amino Acids in the $C_H2$ Domain and Is Modulated by the Hinge Region," J Exp Med., Jun. 1, 1991, 173(6):1483-91.
Dall'Acqua et al., "Properties of human IgG1s engineered for enhanced binding to the neonatal Fc receptor (FcRn)," J Biol Chem., Aug. 18, 2006, 281(33):23514-24. Epub Jun. 21, 2006.

EPO Register Extract EP 1915397 (document submitted in EP opposition and posted by EPO on Feb. 2, 2018); 4 pages.
Geneseq Accession No. AEM45140, Feb. 22, 2007, "Light chain constant region of therapeutic human IgG antibody".
Golay et al., "Mechanism of action of therapeutic monoclonal antibodies: Promises and pitfalls of in vitro and in vivo assays," Archives of Biochemistry and Biophysics, Feb. 25, 2012, 526:146-153.
Hotzel et al., "A strategy for risk mitigation of antibodies with fast clearance," mAbs, Nov.-Dec. 2012, 4(6):753-60. doi: 10.4161/mabs.22189.
Ryman et al., "Pharmacokinetics of Monoclonal Antibodies," CPT Pharmacometrics Syst Pharmacol., Sep. 2017, 6(9):576-588. doi: 10.1002/psp4.12224. Epub Jul. 29, 2017.
Sampei et al., "Identification and multidimensional optimization of an asymmetric bispecific IgG antibody mimicking the function of factor VIII cofactor activity," PLoS One, Feb. 2013, 8(2):e57479. doi: 10.1371/journal.pone.0057479. Epub Feb. 28, 2013.
Stancovski et al., "Mechanistic Aspects of the Opposing Effects of Monoclonal Antibodies to the ERBB2 Receptor on Tumor Growth," Proc Natl Acad Sci USA, Oct. 1, 1991, 88:8691-8695.
Summary of information about antibodies in Examples of patent (document submitted in EP opposition and posted by EPO on Apr. 13, 2018); 3 pages.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol., Jul. 1, 2005, 350(1):126-44.
Yarilin, Fundamentals of Immunology M: Medicina, 1999, pp. 169-72, 354-8 (with English tranlsation), 21 pages.
Yarilin, Fundamentals of Immunology M: Medicina, 1999, pp. 172-74 (with English translation), 8 pages.
U.S. Appl. No. 11/910,128, Igawa et al., filed Oct. 7, 2008.
U.S. Appl. No. 12/295,075, Igawa et al., filed Apr. 20, 2009.
U.S. Appl. No. 12/680,082, Igawa et al., filed Jun. 25, 2010.
U.S. Appl. No. 14/680,250, Igawa et al., filed Apr. 7, 2015.
U.S. Appl. No. 13/497,269, Igawa et al., filed Jun. 1, 2012.
U.S. Appl. No. 15/024,062, Igawa et al., filed Mar. 23, 2016.
U.S. Appl. No. 10/011,858, Igawa et al., issued Jul. 3, 2018.
US Appl. No. 15/782,256, Igawa et al., filed Oct. 12, 2017.
US Appl. No. 12/295,039, Igawa et al., filed Jan. 20, 2009.
U.S. Appl. No. 15/490,936, Igawa et al., filed Apr. 19, 2017.
U.S. Appl. No. 14/741,786, Igawa et al., filed Jun. 17, 2015.
U.S. Appl. No. 15/725,692, Igawa et al., filed Oct. 5, 2017.
U.S. Appl. No. 15/614,842, Igawa et al., filed Jun. 6, 2017.
U.S. Appl. No. 14/962,293, Igawa et al., filed Dec. 8, 2015.
U.S. Appl. No. 13/257,145, Igawa et al., filed Nov. 22, 2011.
U.S. Appl. No. 14/680,250, Igawa et al., filed Apr. 7, 2017.
U.S. Appl. No. 13/497,269, Kuramochi et al., filed Jun. 1, 2012.
U.S. Appl. No. 13/518,861, Igawa et al., filed Oct. 4, 2012.
U.S. Appl. No. 15/617,008, Igawa et al., filed Jun. 8, 2017.
U.S. Appl. No. 15/872,847, Igawa et al., filed Jan. 19, 2018.
U.S. Appl. No. 15/562,186, Igawa et al., filed Sep. 27, 2017.
U.S. Appl. No. 15/024,063, Igawa et al., filed Mar. 23, 2016.
U.S. Appl. No. 16/155,673, Igawa et al, filed Oct. 9, 2018.
Abe et al., "Novel Protein A Resin: Synthetic Polymer Matrix Design Impact on Antibody Binding Capacity," JSR Technical Review No. 119, 2012, p. 1-5 [online], [retrieved on Feb. 17, 2017], retrieved from the internet: <URL:http://www.jsr.co.jp/pdf/rd/tec119-1.pdf > (with English translation).
Cruse et al., Atlas of Immunology, CRC Press LLC, 2004, Chapter 3 "Antigens and Immunogens", p. 109.
Decision of the Opposition Division for EP 2 006 381 on Jul. 25, 2018, 17 pages.
GE Healthcare Life Sciences, Dynamic binding capacity study on MabSelect SuReTM LX for capturing high-titer monoclonal antibodies, Application note 28-9875-25-AA, 2011, [online], [retrieved on Feb. 17, 2017], retrieved from the internet:,http://www.

(56) References Cited

OTHER PUBLICATIONS processdevelopmentforum.com/images/articles/28-9875-25_AA_AN_DBC_study_on_MabSelect_SuRe_LX_final.pdf>.
Geneseq Accession No. ARZ17615, Aug. 21, 2008, "Human antibody IgG2 heavy chain constant region SEQ ID No. 36".
Sampei et al, "Non-antigen-contacting region of an asymmetric bispecific antibody to factors IXa/X significantly affects factor VIII-mimetic activity," mAbs, Jan./Feb. 2015, 7(1):120-8. doi: 10.4161/19420862.2015.989028.
Sequence alignments and modification scheme (document filed during Oral Proceedings in EPO Opposition for EP 2 006 381 and mentioned in minutes of the Oral Proceedings posted by EPO on Jul. 25, 2018); 3 pages.
Van Den Abbeele et al., "Antigen-Binding Site Protection During Radiolabeling Leads to a Higher Immunoreactive Fraction," J Nucl Med, Jan. 1991, 32(1):116-22 A114.
U.S. Appl. No. 16/298,032, Igawa et al., filed Mar. 11, 2019.
Choi et al., "Crystal structures of immunoglobulin Fc heterodimers reveal the molecular basis for heterodimer formation," Mol Immunol, Jun. 2015, 65(2):377-83. doi: 10.1016/j.molimm.2015.02.017. Epub Mar. 2, 2015.
Declaration of Dr. Anette Henriksen, signed Apr. 17, 2019 (submitted by the Opponent during EPO opposition procedure for EP 2 006 381).
Feige et al., "How antibodies fold," Trends Biochem Sci, Apr. 2010, 35(4):189-98. doi:10.1016/j.tibs.2009.11.005. Epub Dec. 21, 2009.
Goulet et al., "Kinetic mechanism of controlled Fab-arm exchange for the formation of bispecific immunoglobulin G1 antibodies," J Biol Chem, Jan. 12, 2018, 293(2):651-661. doi:10.1074/jbc.RA117.000303. Epub Nov. 17, 2017.
Rispens et al., "Mechanism of Immunoglobulin G4 Fab-arm Exchange," J Am Chem Soc, Jul. 6, 2011, 133(26):10302-11. doi: 10.1021/ja203638y. Epub Jun. 15, 2011.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Granted claims of EP 2 275 443 (submitted on May 24, 2019 by the Patentee during EPO Opposition Procedure for EP 2 202 245), 1 page.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted on May 24, 2019 by the Patentee during EPO Opposition Procedure for EP 2 202 245), 4 pages.
U.S. Appl. No. 16/448,088, Igawa et al., filed Jun. 21, 2019.
Barrabes et al., "Effect of sialic acid content on glycoprotein pI analyzed by two-dimensional electrophoresis," Electrophoresis, Sep. 2010, 31(17):2903-12. doi: 10.1002/elps.200900764.
Mariuzza, "The Structural Basis of Antigen-Antibody Recognition," Annu. Rev. Biophys. Biophys. Chem., Jun. 1987, 16:139-159.

* cited by examiner

SEQUENCE LISTING

<160> NUMBER OF SEQ ID NOS: 34

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys

```
            85                  90                  95
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125
```

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 327
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 4
<211> LENGTH: 330
<212> TYPE: PRT
<213> ORGANISM: Artificial
<220> FEATURE:
<223> OTHER INFORMATION: An artificially synthesized peptide sequence

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Phe Leu Gly Gly Pro Ser Val Phe Leu Phe Pro Pro
    115                 120                 125

Lys Pro Lys Asp Thr Leu Met Ile Ser Arg Thr Pro Glu Val Thr Cys
        130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
            165                 170                 175

Glu Gln Phe Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205
```

Lys Gly Leu Pro Ser Ser Ile Glu Lys Thr Ile Ser Lys Ala Lys Gly
            210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Glu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
                325                 330

<210> SEQ ID NO 5
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 6
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

```
Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro

<210> SEQ ID NO 7
<211> LENGTH: 325
<212> TYPE: PRT
<213> ORGANISM: Artificial
<220> FEATURE:
<223> OTHER INFORMATION: An artificially synthesized peptide sequence

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu
            325
```

<210> SEQ ID NO 8
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 8

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Phe Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Glu Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Leu
                325
```

```
<210> SEQ ID NO 9
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 10
<211> LENGTH: 328
<212> TYPE: PRT
<213> ORGANISM: Artificial
<220> FEATURE:
```

<223> OTHER INFORMATION: An artificially synthesized peptide sequence

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 11
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 11

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 12
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 12

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                   55                   60

Leu Ser Ser Val Val Thr Val Pro Ser Ser Ser Leu Gly Thr Gln Thr
 65                  70                   75                   80

Tyr Ile Cys Asn Val Asn His Lys Pro Ser Asn Thr Lys Val Asp Lys
                85                   90                   95

Lys Val Glu Pro Lys Ser Cys Asp Lys Thr His Thr Cys Pro Pro Cys
            100                  105                  110

Pro Ala Pro Glu Ala Ala Gly Gly Pro Ser Val Phe Leu Phe Pro Pro
            115                  120                  125

Lys Pro Lys Asp Thr Leu Met Ile Ser Arg Thr Pro Glu Val Thr Cys
130                  135                  140

Val Val Val Asp Val Ser His Glu Asp Pro Glu Val Lys Phe Asn Trp
145                  150                  155                  160

Tyr Val Asp Gly Val Glu Val His Asn Ala Lys Thr Lys Pro Arg Glu
                165                  170                  175

Glu Gln Tyr Asn Ser Thr Tyr Arg Val Val Ser Val Leu Thr Val Leu
            180                  185                  190

His Gln Asp Trp Leu Asn Gly Lys Glu Tyr Lys Cys Lys Val Ser Asn
            195                  200                  205

Lys Ala Leu Pro Ala Pro Ile Glu Lys Thr Ile Ser Lys Ala Lys Gly
210                  215                  220

Gln Pro Arg Glu Pro Gln Val Tyr Thr Leu Pro Pro Ser Arg Asp Glu
225                  230                  235                  240

Leu Thr Lys Asn Gln Val Ser Leu Thr Cys Leu Val Lys Gly Phe Tyr
                245                  250                  255

Pro Ser Asp Ile Ala Val Glu Trp Glu Ser Asn Gly Gln Pro Glu Asn
            260                  265                  270

Asn Tyr Lys Thr Thr Pro Pro Val Leu Asp Ser Asp Gly Ser Phe Phe
            275                  280                  285

Leu Tyr Ser Lys Leu Thr Val Asp Lys Ser Arg Trp Gln Gln Gly Asn
            290                  295                  300

Val Phe Ser Cys Ser Val Met His Glu Ala Leu His Asn His Tyr Thr
305                  310                  315                  320

Gln Lys Ser Leu Ser Leu Ser Pro
                325

<210> SEQ ID NO 13
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 13

Ala Ser Thr Lys Gly Pro Ser Val Phe Pro Leu Ala Pro Ser Ser Lys
 1               5                   10                   15

Ser Thr Ser Gly Gly Thr Ala Ala Leu Gly Cys Leu Val Lys Asp Tyr
                20                   25                   30

Phe Pro Glu Pro Val Thr Val Ser Trp Asn Ser Gly Ala Leu Thr Ser
            35                   40                   45

Gly Val His Thr Phe Pro Ala Val Leu Gln Ser Ser Gly Leu Tyr Ser
            50                   55                   60

Leu Ser Ser Val Val Thr Val Pro Ser Ser Ser Leu Gly Thr Gln Thr
 65                  70                   75                   80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 14
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Gly Leu Pro Ser Ser Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 15
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Ala His Tyr Thr
305                 310                 315                 320

Gln Lys Ser Leu Ser Leu Ser Pro
                325

<210> SEQ ID NO 16
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175
```

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Gly Leu Pro Ser Ser Ile Glu Lys Thr Ile Ser Lys Ala Lys Gly
        210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Glu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 17
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

```
Lys Gly Leu Pro Ser Ser Ile Glu Lys Thr Ile Ser Lys Ala Lys Gly
            210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Glu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Leu
                325

<210> SEQ ID NO 18
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Asp Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 19
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 19

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Ala Ala Ala Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
```

```
Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro

<210> SEQ ID NO 20
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300
```

```
Ser Val Met His Glu Ala Leu His Asn His Tyr Thr Gln Lys Ser Leu
305                 310                 315                 320

Ser Leu Ser Pro

<210> SEQ ID NO 21
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 21

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Ala Ala Ala Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 22
```

```
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro

<210> SEQ ID NO 23
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 23
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 24
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
                100                 105                 110

Pro Ala Ala Ala Pro Ser Val Phe Leu Phe Pro Pro Lys Pro Lys Asp
                115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro

<210> SEQ ID NO 25
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 25

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
```

```
            65                  70                  75                  80
Tyr Thr Cys Asn Val Asp His Lys Pro Ser Asn Thr Lys Val Asp Lys
                    85                  90                  95

Thr Val Glu Arg Lys Cys Cys Val Glu Cys Pro Pro Cys Pro Ala Pro
                100                 105                 110

Pro Ala Ala Ala Pro Ser Val Phe Leu Phe Pro Pro Lys Pro Lys Asp
                115                 120                 125

Thr Leu Met Ile Ser Arg Thr Pro Glu Val Thr Cys Val Val Val Asp
            130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Glu Gly Asn Val Phe Ser Cys
        290                 295                 300

Ser Val Met His Glu Ala Leu His Ala His Tyr Thr Gln Lys Ser Leu
305                 310                 315                 320

Ser Leu Ser Pro

<210> SEQ ID NO 26
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
                100                 105                 110
```

```
Pro Ala Ala Ala Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Glu Gly Asn Val Phe Ser Cys
            290                 295                 300

Ser Val Met His Glu Ala Leu His Ala His Tyr Thr Gln Lys Ser Leu
305                 310                 315                 320

Ser Leu Ser Pro

<210> SEQ ID NO 27
<211> LENGTH: 119
<212> TYPE: PRT
<213> ORGANISM: Artificial
<220> FEATURE:
<223> OTHER INFORMATION: An artificially synthesized peptide sequence

<400> SEQUENCE: 27

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 28
<211> LENGTH: 107
```

```
<212> TYPE: PRT
<213> ORGANISM: Artificial
<220> FEATURE:
<223> OTHER INFORMATION: An artificially synthesized peptide sequence

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 29
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 29

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 30
<211> LENGTH: 106
<212> TYPE: PRT
<213> ORGANISM: Artificial
<220> FEATURE:
<223> OTHER INFORMATION: An artificially synthesized peptide sequence

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
```

```
                50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Glu Cys
            100                 105

<210> SEQ ID NO 31
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 31

Gln Val Gln Leu Gln Glu Ser Gly Pro Gly Leu Val Arg Pro Ser Gln
 1               5                  10                  15

Thr Leu Ser Leu Thr Cys Thr Val Ser Gly Tyr Ser Ile Thr Ser Asp
                 20                  25                  30

His Ala Trp Ser Trp Val Arg Gln Pro Pro Gly Arg Gly Leu Glu Trp
             35                  40                  45

Ile Gly Tyr Ile Ser Tyr Ser Gly Ile Thr Thr Tyr Asn Pro Ser Leu
 50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
```

```
                305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
                435                 440                 445

<210> SEQ ID NO 32
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 33
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 33

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
```

```
                 370                 375                 380
Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro
                435                 440

<210> SEQ ID NO 34
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 34

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
                210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
```

-continued

```
                290                 295                 300
Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu
                435                 440
```

US 10,435,458 B2

ANTIBODY CONSTANT REGION VARIANTS WITH REDUCED FCGAMMAR BINDING

CROSS-REFERENCE TO RELATED APPLICATIONS

This application is the National Stage of International Application Serial No. PCT/JP2011/055101, filed on Mar. 4, 2011, which claims the benefit of Japanese Patent Application Serial No. 2010-048218, filed on Mar. 4, 2010.

TECHNICAL FIELD

The present invention provides antibody constant regions with an amino acid sequence modified from a naturally-occurring antibody constant region, antibodies comprising such constant regions, pharmaceutical compositions comprising such antibodies, and methods for producing them.

BACKGROUND ART

Antibodies are drawing attention as pharmaceuticals as they are highly stable in blood and have few side effects. Of these, a number of IgG-type antibody pharmaceuticals are available on the market and many antibody pharmaceuticals are currently under development (Non-patent Documents 1 and 2).

Almost all antibody pharmaceuticals currently available on the market are of the IgG1 subclass. IgG1-type antibodies are expected be useful as anti-cancer antibody pharmaceuticals since they can bind to Fcγ receptor and exert ADCC activity. However, when it comes to antibody pharmaceuticals intended for neutralizing biological activity of an antigen, binding of the Fc domain to Fcγ receptor, which is important for effector functions such as ADCC, can cause unnecessary side effects, and thus it is preferable to eliminate such binding activity (Non-patent Document 3). Furthermore, since Fcγ receptor is expressed on antigen-presenting cells, molecules that bind to Fcγ receptor tend to be presented as antigens. It has been reported that antigenicity is and can be enhanced by linking a protein or peptide to the Fc domain of IgG1 (Non-patent Document 4 and Patent Document 1). Interaction between the antibody Fc domain and Fcγ receptor is thought to be a cause of the serious side effects encountered in phase-I clinical trials of TGN1412 (Non-patent Document 5). Thus, binding to Fcγ receptor is considered unfavorable in antibody pharmaceuticals intended for neutralizing the biological activity of an antigen from the perspective of side effects and antigenicity.

A method for impairing the binding to Fcγ receptor is to alter the subtype of the IgG antibody from IgG1 to IgG2 or IgG4; however, this method cannot completely inhibit the binding (Non-patent Document 6). However, the binding to Fcγ receptor is not completely inhibited even if IgG2 or IgG4 is used. One of the methods reported for inhibiting the binding to Fcγ receptor is to artificially alter the Fc domain. For example, the effector functions of anti-CD3 antibodies and anti-CD4 antibodies cause side effects. Thus, amino acids that are not present in the wild-type sequence were introduced into the Fcγ-receptor-binding domain of Fc (Non-patent Documents 3 and 7), and clinical trials are currently being conducted to assess anti-CD3 antibodies and anti-CD4 antibodies that have a mutated Fc domain and do not bind to Fcγ receptor (Non-patent Documents 5 and 8). Alternatively, Fcγ receptor-nonbinding antibodies can be prepared by altering the FcγR-binding sites of IgG1 (positions 233, 234, 235, 236, 327, 330, and 331 in the EU numbering; hereafter abbreviated as position X (EU numbering)) to an IgG2 or IgG4 sequence (Non-patent Document 9 and Patent Document 2). However, there are no reports of constant regions that have completely lost binding to all FcγRs (FcγRI, FcγRIIa, and FcγRIIIa). From the perspective of side-effects, the present inventors constructed constant regions that have completely lost binding to all FcγRs.

Documents of related prior arts for the present invention are described below.

PRIOR ART DOCUMENTS

Patent Documents

[Patent Document 1] US 20050261229 A1
[Patent Document 2] WO 99/58572

Non-Patent Documents

[Non-patent Document 1] Janice M Reichert, Clark J Rosensweig, Laura B Faden & Matthew C Dewitz. Monoclonal antibody successes in the clinic. Nature Biotechnology (2005) 23, 1073-1078
[Non-patent Document 2] Pavlou A K, Belsey M J. The therapeutic antibodies market to 2008. Eur. J. Pharm. Biopharm. 2005 April; 59(3):389-96
[Non-patent Document 3] Reddy M P, Kinney C A, Chaikin M A, Payne A, Fishman-Lobell J, Tsui P, Dal Monte P R, Doyle M L, Brigham-Burke M R, Anderson D, Reff M, Newman R, Hanna N, Sweet R W, Truneh A. Elimination of Fc receptor-dependent effector functions of a modified IgG4 monoclonal antibody to human CD4. J. Immunol. 2000 Feb. 15; 164(4):1925-33
[Non-patent Document 4] Guyre P M, Graziano R F, Goldstein J, Wallace P K, Morganelli P M, Wardwell K, Howell A L. Increased potency of Fc-receptor-targeted antigens. Cancer Immunol. Immunother. 1997 November-December; 45(3-4):146-8
[Non-patent Document 5] Strand V, Kimberly R, Isaacs J D. Biologic therapies in rheumatology: lessons learned, future directions. Nat. Rev. Drug Discov. 2007 January; 6(1):75-92
[Non-patent Document 6] Gessner J E, Heiken H, Tamm A, Schmidt R E. The IgG Fc receptor family. Ann. Hematol. 1998 June; 76(6):231-48
[Non-patent Document 7] Cole M S, Anasetti C, Tso J Y. Human IgG2 variants of chimeric anti-CD3 are nonmitogenic to T cells. J. Immunol. 1997 Oct. 1; 159(7):3613-21
[Non-patent Document 8] Chau L A, Tso J Y, Melrose J, Madrenas J. HuM291(Nuvion), a humanized Fc receptor-nonbinding antibody against CD3, anergizes peripheral blood T cells as partial agonist of the T cell receptor. Transplantation 2001 Apr. 15; 71(7):941-50
[Non-patent Document 9] Armour K L, Clark M R, Hadley A G, Williamson L M. Recombinant human IgG molecules lacking Fcgamma receptor I binding and monocyte triggering activities. Eur. J. Immunol. 1999 August; 29(8): 2613-24

SUMMARY OF THE INVENTION

Problems to be Solved by the Invention

The present invention was achieved in view of the above circumstances. An objective of the present invention is to provide antibody constant regions that have reduced Fcγ receptor-binding activity as a result of altering the amino acids of the antibody constant regions.

Means for Solving the Problems

The present inventors performed dedicated research to create antibody constant regions that have reduced Fcγ receptor-binding activity as a result of altering amino acid sequences of the antibody constant regions. As a result, the present inventors successfully identified novel constant region sequences that have reduced Fcγ receptor-binding activity compared to conventional antibody constant regions.

The present invention provides antibody constant regions with further improvements in safety, risk of antigenicity, and physical properties (stability and homogeneity) as well as superior retention in blood by altering amino acid sequences of the antibody constant regions, antibodies comprising such antibody constant regions, pharmaceutical compositions comprising such antibodies, and methods for producing them.

More specifically, the present invention provides the following:

[1] an antibody constant region of any one of (a) to (m) below:

(a) an antibody constant region comprising an amino acid sequence comprising substitutions of Leu at position 234 (EU numbering), Leu at position 235 (EU numbering), and Asn at position 297 (EU numbering) in the amino acid sequence of SEQ ID NO: 5 (IgG1 constant region) with other amino acids (M112);

(b) an antibody constant region comprising an amino acid sequence comprising substitutions of Leu at position 234 (EU numbering), Leu at position 235 (EU numbering), Ala at position 327 (EU numbering), Ala at position 330 (EU numbering), and Pro at position 331 (EU numbering) in the amino acid sequence of SEQ ID NO: 5 (IgG1 constant region) with other amino acids (M174 or M213);

(c) an antibody constant region comprising an amino acid sequence comprising substitutions of Leu at position 234 (EU numbering), Leu at position 235 (EU numbering), Asn at position 297 (EU numbering), Ala at position 327 (EU numbering), Ala at position 330 (EU numbering), and Pro at position 331 (EU numbering) in the amino acid sequence of SEQ ID NO: 5 (IgG1 constant region) with other amino acids (M220);

(d) an antibody constant region comprising an amino acid sequence comprising substitutions of Leu at position 234 (EU numbering), Leu at position 235 (EU numbering), Ala at position 327 (EU numbering), Ala at position 330 (EU numbering), Pro at position 331 (EU numbering), and Asn at position 434 (EU numbering) in the amino acid sequence of SEQ ID NO: 5 (IgG1 constant region) with other amino acids (M225);

(e) an antibody constant region comprising an amino acid sequence comprising substitutions of Leu at position 234 (EU numbering), Leu at position 235 (EU numbering), Ala at position 327 (EU numbering), Ala at position 330 (EU numbering), Pro at position 331 (EU numbering), His at position 268 (EU numbering), Lys at position 274 (EU numbering), Arg at position 355 (EU numbering), Asp at position 356 (EU numbering), Leu at position 358 (EU numbering), and Gln at position 419 (EU numbering) in the amino acid sequence of SEQ ID NO: 5 (IgG1 constant region) with other amino acids (M226);

(f) an antibody constant region comprising an amino acid sequence comprising substitutions of Phe at position 234 (EU numbering), Leu at position 235 (EU numbering), and Arg at position 409 (EU numbering) in the amino acid sequence of SEQ ID NO: 8 (a constant region having CH1 and Hinge of IgG1, and CH2 and CH3 of IgG4) with other amino acids (M228);

(g) an antibody constant region comprising an amino acid sequence comprising a substitution of Asn at position 297 (EU numbering) in the amino acid sequence of SEQ ID NO: 6 (IgG2 constant region) with another amino acid (M86);

(h) an antibody constant region comprising an amino acid sequence comprising substitutions of Val at position 234 (EU numbering), Gly at position 237 (EU numbering), and Asn at position 297 (EU numbering) in the amino acid sequence of SEQ ID NO: 6 (IgG2 constant region) with other amino acids (M221);

(i) an antibody constant region comprising an amino acid sequence comprising substitutions of Ala at position 330 (EU numbering), Pro at position 331 (EU numbering), and Thr at position 339 (EU numbering) in the amino acid sequence of SEQ ID NO: 6 (IgG2 constant region) with other amino acids (M222);

(j) an antibody constant region comprising an amino acid sequence comprising substitutions of Val at position 234 (EU numbering), Gly at position 237 (EU numbering), Ala at position 330 (EU numbering), Pro at position 331 (EU numbering), and Thr at position 339 (EU numbering) in the amino acid sequence of SEQ ID NO: 6 (IgG2 constant region) with other amino acids (M223);

(k) an antibody constant region comprising an amino acid sequence comprising substitutions of Val at position 234 (EU numbering), Gly at position 237 (EU numbering), Ala at position 330 (EU numbering), Pro at position 331 (EU numbering), Thr at position 339 (EU numbering), and Asn at position 297 (EU numbering) in the amino acid sequence of SEQ ID NO: 6 (IgG2 constant region) with other amino acids (M224);

(l) an antibody constant region comprising an amino acid sequence comprising substitutions of His at position 268 (EU numbering), Arg at position 355 (EU numbering), Gln at position 419 (EU numbering), and Asn at position 434 (EU numbering) in the amino acid sequence of SEQ ID NO: 6 (IgG2 constant region) with other amino acids (M211); or (m) an antibody constant region comprising an amino acid sequence comprising substitutions of His at position 268 (EU numbering), Arg at position 355 (EU numbering), Gln at position 419 (EU numbering), Asn at position 434 (EU numbering), Cys at position 131 (EU numbering), Arg at position 133 (EU numbering), Glu at position 137 (EU numbering), Ser at position 138 (EU numbering), and Cys at position 220 (EU numbering) in the amino acid sequence of SEQ ID NO: 6 (IgG2 constant region) with other amino acids (M209);

[2] an antibody constant region of any one of (A) to (M) below:

(A) an antibody constant region comprising an amino acid sequence comprising substitutions of Ala for Leu at position 234 (EU numbering), Ala for Leu at position 235 (EU numbering), and Ala for Asn at position 297

(EU numbering) in the amino acid sequence of SEQ ID NO: 5 (IgG1 constant region) (M112);

(B) an antibody constant region comprising an amino acid sequence comprising substitutions of Ala for Leu at position 234 (EU numbering), Ala or Asp for Leu at position 235 (EU numbering), Gly for Ala at position 327 (EU numbering), Ser for Ala at position 330 (EU numbering), and Ser for Pro at position 331 (EU numbering) in the amino acid sequence of SEQ ID NO: 5 (IgG1 constant region) (M174 or M213);

(C) an antibody constant region comprising an amino acid sequence comprising substitutions of Ala for Leu at position 234 (EU numbering), Ala for Leu at position 235 (EU numbering), Ala for Asn at position 297 (EU numbering), Gly for Ala at position 327 (EU numbering), Ser for Ala at position 330 (EU numbering), and Ser for Pro at position 331 (EU numbering) in the amino acid sequence of SEQ ID NO: 5 (IgG1 constant region) (M220);

(D) an antibody constant region comprising an amino acid sequence comprising substitutions of Ala for Leu at position 234 (EU numbering), Ala for Leu at position 235 (EU numbering), Gly for Ala at position 327 (EU numbering), Ser for Ala at position 330 (EU numbering), Ser for Pro at position 331 (EU numbering), and Ala for Asn at position 434 (EU numbering) in the amino acid sequence of SEQ ID NO: 5 (IgG1 constant region) (M225);

(E) an antibody constant region comprising an amino acid sequence comprising substitutions of Ala for Leu at position 234 (EU numbering), Ala for Leu at position 235 (EU numbering), Gly for Ala at position 327 (EU numbering), Ser for Ala at position 330 (EU numbering), Ser for Pro at position 331 (EU numbering), Gln for His at position 268 (EU numbering), Gln for Lys at position 274 (EU numbering), Gln for Arg at position 355 (EU numbering), Glu for Asp at position 356 (EU numbering), Met for Leu at position 358 (EU numbering), and Glu for Gln at position 419 (EU numbering) in the amino acid sequence of SEQ ID NO: 5 (IgG1 constant region) (M226);

(F) an antibody constant region comprising an amino acid sequence comprising substitutions of Ala for Phe at position 234 (EU numbering), Ala for Leu at position 235 (EU numbering), and Lys for Arg at position 409 (EU numbering) in the amino acid sequence of SEQ ID NO: 8 (a constant region having CH1 and Hinge of IgG1, and CH2 and CH3 of IgG4) (M228);

(G) an antibody constant region comprising an amino acid sequence comprising a substitution of Ala for Asn at position 297 (EU numbering) in the amino acid sequence of SEQ ID NO: 6 (IgG2 constant region) (M86);

(H) an antibody constant region comprising an amino acid sequence comprising substitutions of Ala for Val at position 234 (EU numbering), Ala for Gly at position 237 (EU numbering), and Ala for Asn at position 297 (EU numbering) in the amino acid sequence of SEQ ID NO: 6 (IgG2 constant region) (M221);

(I) an antibody constant region comprising an amino acid sequence comprising substitutions of Ser for Ala at position 330 (EU numbering), Ser for Pro at position 331 (EU numbering), and Ala for Thr at position 339 (EU numbering) in the amino acid sequence of SEQ ID NO: 6 (IgG2 constant region) (M222);

(J) an antibody constant region comprising an amino acid sequence comprising substitutions of Ala for Val at position 234 (EU numbering), Ala for Gly at position 237 (EU numbering), Ser for Ala at position 330 (EU numbering), Ser for Pro at position 331 (EU numbering), and Ala for Thr at position 339 (EU numbering) in the amino acid sequence of SEQ ID NO: 6 (IgG2 constant region) (M223);

(K) an antibody constant region comprising an amino acid sequence comprising substitutions of Ala for Val at position 234 (EU numbering), Ala for Gly at position 237 (EU numbering), Ser for Ala at position 330 (EU numbering), Ser for Pro at position 331 (EU numbering), Ala for Thr at position 339 (EU numbering), and Ala for Asn at position 297 (EU numbering) in the amino acid sequence of SEQ ID NO: 6 (IgG2 constant region) (M224);

(L) an antibody constant region comprising an amino acid sequence comprising substitutions of Gln for His at position 268 (EU numbering), Gln for Arg at position 355 (EU numbering), Glu for Gln at position 419 (EU numbering), and Ala for Asn at position 434 (EU numbering) in the amino acid sequence of SEQ ID NO: 6 (IgG2 constant region) (M211); or (M) an antibody constant region comprising an amino acid sequence comprising substitutions of Gln for His at position 268 (EU numbering), Gln for Arg at position 355 (EU numbering), Glu for Gln at position 419 (EU numbering), Ala for Asn at position 434 (EU numbering), Ser for Cys at position 131 (EU numbering), Lys for Arg at position 133 (EU numbering), Gly for Glu at position 137 (EU numbering), Gly for Ser at position 138 (EU numbering), and Ser for Cys at position 220 (EU numbering) in the amino acid sequence of SEQ ID NO: 6 (IgG2 constant region) (M209);

[3] an antibody constant region of any one of (1) to (14) below:
(1) an antibody constant region comprising the amino acid sequence of SEQ ID NO: 11 (M112);
(2) an antibody constant region comprising the amino acid sequence of SEQ ID NO: 13 (M174);
(3) an antibody constant region comprising the amino acid sequence of SEQ ID NO: 14 (M220);
(4) an antibody constant region comprising the amino acid sequence of SEQ ID NO: 15 (M225);
(5) an antibody constant region comprising the amino acid sequence of SEQ ID NO: 16 (M226);
(6) an antibody constant region comprising the amino acid sequence of SEQ ID NO: 17 (M228);
(7) an antibody constant region comprising the amino acid sequence of SEQ ID NO: 18 (M213);
(8) an antibody constant region comprising the amino acid sequence of SEQ ID NO: 20 (M86);
(9) an antibody constant region comprising the amino acid sequence of SEQ ID NO: 21 (M221);
(10) an antibody constant region comprising the amino acid sequence of SEQ ID NO: 22 (M222);
(11) an antibody constant region comprising the amino acid sequence of SEQ ID NO: 23 (M223);
(12) an antibody constant region comprising the amino acid sequence of SEQ ID NO: 24 (M224);
(13) an antibody constant region comprising the amino acid sequence of SEQ ID NO: 25 (M211); or
(14) an antibody constant region comprising the amino acid sequence of SEQ ID NO: 26 (M209);

[4] an antibody comprising the antibody constant region of any one of [1] to [3]; and

[5] a pharmaceutical composition comprising the antibody of [4].

MODE FOR CARRYING OUT THE INVENTION

Figure 1:
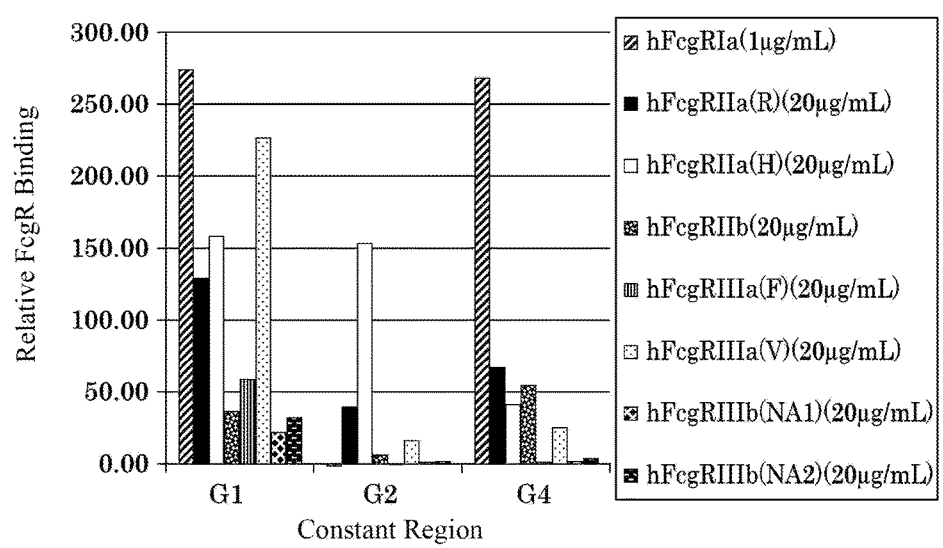
FIG. 1 shows comparison of the amount of FcγR binding by H0-G1d/L0-k0, H0-G2d/L0-k0, and H0-G4d/L0-k0.

The present invention provides antibody constant regions with an amino acid sequence modified from a naturally-occurring antibody constant region, antibodies comprising such constant regions, pharmaceutical compositions comprising such antibodies, and methods for producing them.

The antibody heavy-chain constant regions include IgG1-, IgG2-, IgG3-, and IgG4-type constant regions. In the present invention, there is no particular limitation on the heavy-chain constant region; however, it is preferably a human heavy chain constant region. Human IgG1 or human IgG2 constant regions are particularly preferred in the present invention. The human heavy-chain constant regions of the present invention may be heavy-chain constant regions combined from two or more different types of heavy-chain constant regions. Examples of such heavy-chain constant regions combined from two or more types of heavy chain constant regions include heavy-chain constant regions in which the CH1 domain and hinge region are derived from human IgG1, and the CH2 and CH3 domains are derived from human IgG4.

Amino acid sequences of heavy-chain constant regions are known to those skilled in the art. The amino acids of the human IgG1 constant region are shown in SEQ ID NO: 1. The amino acid sequence of the human IgG2 constant region is shown in SEQ ID NO:2. The amino acid sequence of the human IgG4 constant region is shown in SEQ ID NO: 3. The amino acid sequence of a heavy-chain constant region in which the CH1 domain and hinge region are derived from human IgG1, and the CH2 and CH3 domains are derived from human IgG4 is shown in SEQ ID NO: 4. In the present invention, the constant region may lack C-terminal Gly and Lys. A human IgG1 constant region in which C-terminal Gly and Lys have been deleted is shown in SEQ ID NO: 5. A human IgG2 constant region in which C-terminal Gly and Lys have been deleted is shown in SEQ ID NO: 6. A human IgG4 constant region in which C-terminal Gly and Lys have been deleted is shown in SEQ ID NO: 7. A constant region in which C-terminal Gly and Lys have been deleted, the CH1 domain and hinge region are derived from human IgG1, and the CH2 and CH3 domains are derived from human IgG4 is shown in SEQ ID NO: 8. In the present invention, a constant region in which C-terminal Gly and Lys have been deleted can be substituted with a constant region in which C-terminal Gly and Lys have not been deleted. More specifically, in this specification, the amino acid sequence of SEQ ID NO: 5 which is an IgG1 constant region with deletions of C-terminal Gly and Lys can be substituted with the amino acid sequence of SEQ ID NO: 1 which is an IgG1 constant region that does not have C-terminal Gly and Lys deletions. The amino acid sequence of SEQ ID NO: 6 which is an IgG2 constant region with deletions of C-terminal Gly and Lys can be substituted with the amino acid sequence of SEQ ID NO: 2 which is an IgG2 constant region that does not have C-terminal Gly and Lys deletions. The amino acid sequence of SEQ ID NO: 7 which is an IgG4 constant region with deletions of C-terminal Gly and Lys can be substituted with the amino acid sequence of SEQ ID NO: 3 which is an IgG4 constant region that does not have C-terminal Gly and Lys deletions. The amino acid sequence of SEQ ID NO: 8 which is an IgG1/IgG4 constant region with deletions of C-terminal Gly and Lys can be substituted with the amino acid sequence of SEQ ID NO: 4 which is an IgG1/IgG4 constant region that does not have C-terminal Gly and Lys deletions. Alternatively, constant regions used in the present invention may be constant regions with deletion of either one of C-terminal Gly and Lys. Multiple allotype sequences of human IgG2 constant regions based on gene polymorphisms are described in the "Sequences of proteins of immunological interest", NIH Publication No. 91-3242. Any of these sequences may be used in the present invention. For constant regions other than the human IgG2 (human IgG1, human IgG4, etc.) type, any allotype of the existing multiple allotypes can be used.

Antibody constant regions of the present invention with amino acid alterations (substitutions, deletions, additions, and/or insertions) may include other amino acid alterations or modifications as long as they include the amino acid alterations of the present invention.

Specifically, constant regions comprising the alterations below are all included in the present invention.
  Alterations based on the present invention are introduced into the amino acid sequence of SEQ ID NO: 1 (human IgG1 constant region).
  Alterations based on the present invention are introduced into an altered amino acid sequence derived from SEQ ID NO: 5 (human IgG1 constant region).
  Alterations based on the present invention are introduced into the amino acid sequence of SEQ ID NO: 1 (human IgG1 constant region), and additional alterations are further introduced.

Similarly, constant regions comprising alterations such as those below are also included in the present invention.
  Alterations based on the present invention are introduced into the amino acid sequence of SEQ ID NO: 2 (human IgG2 constant region).
  Alterations based on the present invention are introduced into an altered amino acid sequence derived from SEQ ID NO: 6 (human IgG2 constant region).
  Alterations based on the present invention are introduced into the amino acid sequence of SEQ ID NO: 2 (human IgG2 constant region), and additional alterations are further introduced.

Similarly, constant regions comprising alterations such as those below are also included in the present invention.
  Alterations based on the present invention are introduced into the amino acid sequence of SEQ ID NO: 4 (a constant region having CH1 and Hinge of IgG1, and CH2 and CH3 of IgG4, i.e., human IgG1/IgG4 constant region).
  Alterations based on the present invention are introduced into an altered amino acid sequence of SEQ ID NO: 8

(a constant region having CH1 and Hinge of IgG1, and CH2 and CH3 of IgG4, i.e., human IgG1/IgG4 constant region).

Alterations based on the present invention are introduced into the amino acid sequence of SEQ ID NO: 4 (a constant region having CH1 and Hinge of IgG1, and CH2 and CH3 of IgG4, i.e., human IgG1/IgG4 constant region), and additional alterations are further introduced.

Furthermore, when the constant regions are bound by sugar chains, the chains may have any structure. For example, the sugar chain at position 297 (EU numbering) may have any sugar chain structure (the sugar chain is preferably fucosylated). Alternatively, the constant regions may have no sugar chain (for example, they can be produced in *Escherichia coli*).

<IgG1 Constant Regions with Amino Acid Alterations>

The present invention provides heavy-chain constant regions with an altered binding activity towards an Fcγ receptor (FcγR) and/or FcRn compared to human IgG1 constant regions having naturally-occurring amino acid sequences. When the FcγR-binding activity is altered compared to that of a human IgG1 constant region having a naturally-occurring amino acid sequence, it is preferable that the FcγR-binding activity is reduced. When the FcRn-binding activity is altered compared to that of a human IgG1 constant region having a naturally-occurring amino acid sequence, it is preferable that the FcRn-binding activity is increased.

(M112)

The present invention provides antibody constant regions comprising an amino acid sequence comprising substitutions of Leu at position 234 (EU numbering), Leu at position 235 (EU numbering), and Asn at position 297 (EU numbering) in the amino acid sequence of SEQ ID NO: 5 (IgG1 constant region) with other amino acids.

There is no particular limitation on the amino acids after substitution; however, substitutions of Ala for Leu at position 234 (EU numbering), Ala for Leu at position 235 (EU numbering), and Ala for Asn at position 297 (EU numbering) are preferred. Examples of such heavy-chain constant regions include heavy-chain constant regions comprising the amino acid sequence of SEQ ID NO: 11 (M112).

The FcγR-binding activity can be reduced by performing these substitutions.

Heavy-chain constant regions provided by the present invention may comprise at least the amino acid substitutions described above. They may also comprise other amino acid alterations (such as substitutions, deletions, additions, and/or insertions) or modifications.

(M174 and M213)

The present invention provides antibody constant regions comprising an amino acid sequence comprising substitutions of Leu at position 234 (EU numbering), Leu at position 235 (EU numbering), Ala at position 327 (EU numbering), Ala at position 330 (EU numbering), and Pro at position 331 (EU numbering) in the amino acid sequence of SEQ ID NO: 5 (IgG1 constant region) with other amino acids.

There is no particular limitation on the amino acids after substitution; however, substitutions of Ala for Leu at position 234 (EU numbering), Ala or Asp for Leu at position 235 (EU numbering), Gly for Ala at position 327 (EU numbering), Ser for Ala at position 330 (EU numbering), and Ser for Pro at position 331 (EU numbering) are preferred. Examples of such heavy-chain constant regions include heavy-chain constant regions comprising the amino acid sequence of SEQ ID NO: 13 (M174) and heavy-chain constant regions comprising the amino acid sequence of SEQ ID NO: 18 (M213).

The FcγR-binding activity can be reduced by performing these substitutions.

Heavy-chain constant regions provided by the present invention may comprise at least the amino acid substitutions described above. They may also comprise other amino acid alterations (such as substitutions, deletions, additions, and/or insertions) or modifications.

(M220)

Examples of antibody constant regions comprising the above-mentioned amino acid alterations include antibody constant regions further comprising substitution of Asn at position 297 (EU numbering) with another amino acid in addition to the above-mentioned alterations. Therefore, the present invention provides antibody constant regions comprising an amino acid sequence comprising substitutions of Leu at position 234 (EU numbering), Leu at position 235 (EU numbering), Asn at position 297 (EU numbering), Ala at position 327 (EU numbering), Ala at position 330 (EU numbering), and Pro at position 331 (EU numbering) in the amino acid sequence of SEQ ID NO: 5 (IgG1 constant region) with other amino acids.

There is no particular limitation on the amino acids after substitution; however, substitutions of Ala for Leu at position 234 (EU numbering), Ala for Leu at position 235 (EU numbering), Ala for Asn at position 297 (EU numbering), Gly for Ala at position 327 (EU numbering), Ser for Ala at position 330 (EU numbering), and Ser for Pro at position 331 (EU numbering) are preferred. Examples of such heavy-chain constant regions include heavy-chain constant regions comprising the amino acid sequence of SEQ ID NO: 14 (M220).

The FcγR-binding activity can be reduced by performing these substitutions.

Heavy-chain constant regions provided by the present invention may comprise at least the above-described amino acid substitutions. They may also comprise other amino acid alterations (such as substitutions, deletions, additions, and/or insertions) or modifications.

(M225)

Other examples of antibody constant regions comprising the above-mentioned amino acid alterations include antibody constant regions further comprising substitution of Asn at position 434 (EU numbering) with another amino acid in addition to the above-mentioned alterations. Therefore, the present invention provides antibody constant regions comprising an amino acid sequence comprising substitutions of Leu at position 234 (EU numbering), Leu at position 235 (EU numbering), Ala at position 327 (EU numbering), Ala at position 330 (EU numbering), Pro at position 331 (EU numbering), and Asn at position 434 (EU numbering) in the amino acid sequence of SEQ ID NO: 5 (IgG1 constant region) with other amino acids.

There is no particular limitation on the amino acids after substitution; however, substitutions of Ala for Leu at position 234 (EU numbering), Ala for Leu at position 235 (EU numbering), Gly for Ala at position 327 (EU numbering), Ser for Ala at position 330 (EU numbering), Ser for Pro at position 331 (EU numbering), and Ala for Asn at position 434 (EU numbering) are preferred. Examples of such heavy-chain constant regions include heavy-chain constant regions comprising the amino acid sequence of SEQ ID NO: 15 (M225).

The FcγR-binding activity can be reduced by performing these substitutions. Furthermore, the FcRn-binding activity can be increased by performing these substitutions.

Heavy-chain constant regions provided by the present invention may comprise at least the above-described amino acid substitutions. They may also comprise other amino acid alterations (such as substitutions, deletions, additions, and/or insertions) or modifications.

(M226)

Other examples of antibody constant regions comprising the above-mentioned amino acid alterations include antibody constant regions further comprising substitutions of His at position 268 (EU numbering), Lys at position 274 (EU numbering), Arg at position 355 (EU numbering), Asp at position 356 (EU numbering), Leu at position 358 (EU numbering), and Gln at position 419 (EU numbering) with other amino acids in addition to the above-mentioned alterations. Therefore, the present invention provides antibody constant regions comprising an amino acid sequence comprising substitutions of Leu at position 234 (EU numbering), Leu at position 235 (EU numbering), Ala at position 327 (EU numbering), Ala at position 330 (EU numbering), Pro at position 331 (EU numbering), His at position 268 (EU numbering), Lys at position 274 (EU numbering), Arg at position 355 (EU numbering), Asp at position 356 (EU numbering), Leu at position 358 (EU numbering), and Gln at position 419 (EU numbering) in the amino acid sequence of SEQ ID NO: 5 (IgG1 constant region) with other amino acids.

There is no particular limitation on the amino acids after substitution; however, substitutions of Ala for Leu at position 234 (EU numbering), Ala for Leu at position 235 (EU numbering), Gly for Ala at position 327 (EU numbering), Ser for Ala at position 330 (EU numbering), Ser for Pro at position 331 (EU numbering), Gln for His at position 268 (EU numbering), Gln for Lys at position 274 (EU numbering), Gln for Arg at position 355 (EU numbering), Glu for Asp at position 356 (EU numbering), Met for Leu at position 358 (EU numbering), and Glu for Gln at position 419 (EU numbering) are preferred. Examples of such heavy-chain constant regions include heavy-chain constant regions comprising the amino acid sequence of SEQ ID NO: 16 (M226).

The FcγR-binding activity can be reduced by performing these substitutions.

Heavy-chain constant regions provided by the present invention may comprise at least the above-described amino acid substitutions. They may also comprise other amino acid alterations (such as substitutions, deletions, additions, and/or insertions) or modifications.

(M228)

The present invention provides antibody constant regions comprising an amino acid sequence comprising substitutions of Phe at position 234 (EU numbering), Leu at position 235 (EU numbering), and Arg at position 409 (EU numbering) in the amino acid sequence of SEQ ID NO: 8 (a constant region having CH1 and Hinge of IgG1, and CH2 and CH3 of IgG4) with other amino acids.

There is no particular limitation on the amino acids after substitution; however, substitutions of Ala for Leu at position 234 (EU numbering), Ala for Leu at position 235 (EU numbering), and Lys for Arg at position 409 (EU numbering) are preferred. Examples of such heavy-chain constant regions include heavy-chain constant regions comprising the amino acid sequence of SEQ ID NO: 17 (M228).

The FcγR-binding activity can be reduced by performing these substitutions.

Heavy-chain constant regions provided by the present invention may comprise at least the above-described amino acid substitutions. They may also comprise other amino acid alterations (such as substitutions, deletions, additions, and/or insertions) or modifications.

(M86)

The present invention provides antibody constant regions comprising an amino acid sequence comprising substitution of Asn at position 297 (EU numbering) in the amino acid sequence of SEQ ID NO: 6 (IgG2 constant region) with another amino acid.

There is no particular limitation on the amino acid after substitution; however, substitution of Ala for Asn at position 297 (EU numbering) is preferred. Examples of such heavy-chain constant regions include heavy-chain constant regions comprising the amino acid sequence of SEQ ID NO: 20 (M86).

The FcγR-binding activity can be reduced by performing this substitution.

Heavy-chain constant regions provided by the present invention may comprise at least the above-described amino acid substitution. They may also comprise other amino acid alterations (such as substitutions, deletions, additions, and/or insertions) or modifications.

(M221)

Examples of antibody constant regions comprising the above-mentioned amino acid alterations include antibody constant regions further comprising substitutions of Val at position 234 (EU numbering) and Gly at position 237 (EU numbering) with other amino acids in addition to the above-mentioned alterations. Therefore, the present invention provides antibody constant regions comprising an amino acid sequence comprising substitutions of Val at position 234 (EU numbering), Gly at position 237 (EU numbering), and Asn at position 297 (EU numbering) in the amino acid sequence of SEQ ID NO: 6 (IgG2 constant region) with other amino acids.

There is no particular limitation on the amino acids after substitution; however, substitutions of Ala for Val at position 234 (EU numbering), Ala for Gly at position 237 (EU numbering), and Ala for Asn at position 297 (EU numbering) are preferred. Examples of such heavy chain constant regions include heavy chain constant regions comprising the amino acid sequence of SEQ ID NO: 21 (M221).

The FcγR-binding activity can be reduced by performing these substitutions.

Heavy-chain constant regions provided by the present invention may comprise at least the above-described amino acid substitutions. They may also comprise other amino acid alterations (such as substitutions, deletions, additions, and/or insertions) or modifications.

(M222)

The present invention provides antibody constant regions comprising an amino acid sequence comprising substitutions of Ala at position 330 (EU numbering), Pro at position 331 (EU numbering), and Thr at position 339 (EU numbering) in the amino acid sequence of SEQ ID NO: 6 (IgG2 constant region) with other amino acids.

There is no particular limitation on the amino acids after substitution; however, substitutions of Ser for Ala at position 330 (EU numbering), Ser for Pro at position 331 (EU numbering), and Ala for Thr at position 339 (EU numbering) are preferred. Examples of such heavy-chain constant regions include heavy-chain constant regions comprising the amino acid sequence of SEQ ID NO: 22 (M222).

The FcγR-binding activity can be reduced by performing these substitutions.

Heavy-chain constant regions provided by the present invention may comprise at least the above-described amino acid substitutions. They may also comprise other amino acid alterations (such as substitutions, deletions, additions, and/or insertions) or modifications.

(M223)

Examples of antibody constant regions comprising the above-mentioned amino acid alterations include antibody constant regions further comprising substitutions of Val at position 234 (EU numbering) and Gly at position 237 (EU numbering) with other amino acids in addition to the above-mentioned alterations. Therefore, the present invention provides antibody constant regions comprising an amino acid sequence comprising substitutions of Val at position 234 (EU numbering), Gly at position 237 (EU numbering), Ala at position 330 (EU numbering), Pro at position 331 (EU numbering), and Thr at position 339 (EU numbering) in the amino acid sequence of SEQ ID NO: 6 (IgG2 constant region) with other amino acids.

There is no particular limitation on the amino acids after substitution; however, substitutions of Ala for Val at position 234 (EU numbering), Ala for Gly at position 237 (EU numbering), Ser for Ala at position 330 (EU numbering), Ser for Pro at position 331 (EU numbering), and Ala for Thr at position 339 (EU numbering) are preferred. Examples of such heavy-chain constant regions include heavy-chain constant regions comprising the amino acid sequence of SEQ ID NO: 23 (M223).

The FcγR-binding activity can be reduced by performing these substitutions.

Heavy-chain constant regions provided by the present invention may comprise at least the above-described amino acid substitutions. They may also comprise other amino acid alterations (such as substitutions, deletions, additions, and/or insertions) or modifications.

(M224)

Examples of antibody constant regions comprising the above-mentioned amino acid alterations include antibody constant regions further comprising substitutions of Val at position 234 (EU numbering) and Gly at position 237 (EU numbering) with other amino acids in addition to the above-mentioned alterations. Therefore, the present invention provides antibody constant regions comprising an amino acid sequence comprising substitutions of Val at position 234 (EU numbering), Gly at position 237 (EU numbering), Asn at position 297 (EU numbering), Ala at position 330 (EU numbering), Pro at position 331 (EU numbering), and Thr at position 339 (EU numbering) in the amino acid sequence of SEQ ID NO: 6 (IgG2 constant region) with other amino acids.

There is no particular limitation on the amino acids after substitution; however, substitutions of Ala for Val at position 234 (EU numbering), Ala for Gly at position 237 (EU numbering); Ala for Asn at position 297 (EU numbering), Ser for Ala at position 330 (EU numbering), Ser for Pro at position 331 (EU numbering), and Ala for Thr at position 339 (EU numbering) are preferred. Examples of such heavy-chain constant regions include heavy-chain constant regions comprising the amino acid sequence of SEQ ID NO: 24 (M224).

The FcγR-binding activity can be reduced by performing these substitutions.

Heavy-chain constant regions provided by the present invention may comprise at least the above-described amino acid substitutions. They may also comprise other amino acid alterations (such as substitutions, deletions, additions, and/or insertions) or modifications.

(M211)

The present invention provides antibody constant regions comprising an amino acid sequence comprising substitutions of His at position 268 (EU numbering), Arg at position 355 (EU numbering), Gln at position 419 (EU numbering), and Asn at position 434 (EU numbering) in the amino acid sequence of SEQ ID NO: 6 (IgG2 constant region) with other amino acids.

There is no particular limitation on the amino acids after substitution; however, substitutions of Gln for His at position 268 (EU numbering), Gln for Arg at position 355 (EU numbering), Glu for Gln at position 419 (EU numbering), and Ala for Asn at position 434 (EU numbering) are preferred. Examples of such heavy-chain constant regions include heavy-chain constant regions comprising the amino acid sequence of SEQ ID NO: 25 (M211).

The FcγR-binding activity can be reduced by performing these substitutions. Furthermore, the isoelectric point can be lowered by performing these substitutions. Also, the FcRn-binding activity can be increased by performing these substitutions.

Heavy-chain constant regions provided by the present invention may comprise at least the above-described amino acid substitutions. They may also comprise other amino acid alterations (such as substitutions, deletions, additions, and/or insertions) or modifications.

(M209)

Examples of antibody constant regions comprising the above-mentioned amino acid alterations include antibody constant regions further comprising substitutions of Cys at position 131 (EU numbering), Arg at position 133 (EU numbering), Glu at position 137 (EU numbering), Ser at position 138 (EU numbering), and Cys at position 220 (EU numbering) with other amino acids in addition to the above-mentioned alterations. Therefore, the present invention provides antibody constant regions comprising an amino acid sequence comprising substitutions of His at position 268 (EU numbering), Arg at position 355 (EU numbering), Gln at position 419 (EU numbering), Asn at position 434 (EU numbering), Cys at position 131 (EU numbering), Arg at position 133 (EU numbering), Glu at position 137 (EU numbering), Ser at position 138 (EU numbering), and Cys at position 220 (EU numbering) in the amino acid sequence of SEQ ID NO: 6 (IgG2 constant region) with other amino acids. Instead of substituting Cys at position 220 (EU numbering) with another amino acid, one can substitute Cys at position 219 (EU numbering) with another amino acid.

There is no particular limitation on the amino acids after substitution; however, substitutions of Gln for His at position 268 (EU numbering), Gln for Arg at position 355 (EU numbering), Glu for Gln at position 419 (EU numbering), Ala for Asn at position 434 (EU numbering), Ser for Cys at position 131 (EU numbering), Lys for Arg at position 133 (EU numbering), Gly for Glu at position 137 (EU numbering), Gly for Ser at position 138 (EU numbering), and Ser for Cys at position 220 (EU numbering) are preferred. When the substitution is at position 219 (EU numbering) rather than at position 220 (EU numbering), Cys at position 219 (EU numbering) is Ser. Examples of such heavy-chain constant regions include heavy-chain constant regions comprising the amino acid sequence of SEQ ID NO: 26 (M209).

The FcγR-binding activity can be reduced by performing these substitutions. Furthermore, the isoelectric point can be lowered by performing these substitutions. Also, the FcRn-binding activity can be increased by performing these substitutions. In addition, heterogeneous components can be reduced by performing these substitutions.

Heavy-chain constant regions provided by the present invention may comprise at least the above-described amino acid substitutions. They may also comprise other amino acid alterations (such as substitutions, deletions, additions, and/or insertions) or modifications.

Furthermore, the present invention provides antibodies comprising any one of the above heavy-chain constant regions. When a light-chain constant region is comprised in an antibody of the present invention, the light-chain constant region may be any light-chain constant region. For example, a light-chain constant region comprising a naturally-occurring amino acid sequence may be used. Alternatively, a variant with one or more amino acid substitutions, deletions, additions, and/or insertions in the amino acid sequence of a naturally-occurring light chain constant region may be used.

Examples of variants of a light-chain constant region include light chain constant regions comprising the amino acid sequence of SEQ ID NO: 30 (k3).

Amino acid modifications of the present invention include post-translational modifications. For example, modification of N-terminal glutamine in a variable region to pyroglutamic acid by pyroglutamylation is a post-translational modification well known to those skilled in the art. Therefore, when the N terminus of the heavy chain of an antibody of the present invention is glutamine, an antibody comprising a variable region in which the glutamine is modified to pyroglutamic acid is included in the present invention.

Other examples of post-translational modifications include addition or deletion of sugar chains. For example, in the IgG1 constant region consisting of the amino acid sequence of SEQ ID NO: 11, the amino acid residue at position 297 (EU numbering) may be modified by sugar chains. The sugar chain structures involved in the modification are not limited. In general, antibodies expressed in eukaryotic cells include sugar chain modifications in the constant regions. Therefore, antibodies expressed in cells such as those below are usually modified by some kind of sugar chain:

antibody-producing cells of mammals; and eukaryotic cells transformed with an expression vector containing an antibody-encoding DNA.

Eukaryotic cells indicated herein include yeast and animal cells. For example, CHO cells and HEK293H cells are representative animal cells for transformation using expression vectors containing an antibody-encoding DNA. Those without sugar chain modification at this position are also included in the constant regions of the present invention. Antibodies in which the constant regions are not modified by sugar chains can be obtained by expressing the antibody-encoding gene in prokaryotic cells such as *Escherichia coli*.

More specifically, for example, sialic acid may be added to the sugar chain of the Fc region (MAbs. 2010 September-October; 2(5):519-27).

There is no limitation on the antigen type, antibody form, antibody source, and such in the present invention, and they may be any antibodies as long as they comprise the above heavy-chain constant regions. While they may be monoclonal antibodies (including full-length monoclonal antibodies) or polyclonal antibodies, monoclonal antibodies are preferred. There is no particular limitation on the source of the antibodies, and they include human antibodies, mouse antibodies, rat antibodies, and rabbit antibodies. With respect to the form, antibodies of the present invention may include antibody mutants, antibody fragments, multi-specific antibodies (for example, bispecific antibodies), chimeric antibodies, humanized antibodies, and complete humanized antibodies. In a preferred embodiment, the antibodies of the present invention include humanized antibodies and human antibodies.

A humanized antibody is also called a reshaped human antibody. Specifically, humanized antibodies prepared by grafting the CDRs of a non-human animal antibody such as a mouse antibody to a human antibody and such are known. Common genetic engineering techniques for obtaining humanized antibodies are also known. Specifically, for example, overlap extension PCR is known as a method for grafting mouse antibody CDRs to human FRs.

A vector for expressing a humanized antibody can be produced by inserting a DNA encoding an antibody variable region in which three CDRs and four FRs are ligated and a DNA encoding a human antibody constant region into an expression vector so that these DNAs are fused in frame. After this integration vector is transfected into a host to establish recombinant cells, these cells are cultured, and the DNA encoding the humanized antibody is expressed to produce the humanized antibody in the culture of the cells (see, European Patent Publication No. EP 239,400, and International Patent Publication No. WO 1996/002576).

As necessary, an amino acid residue in an FR may be substituted so that the CDRs of a reshaped human antibody form an appropriate antigen-binding site. For example, a mutation can be introduced into the amino acid sequence of an FR by applying the PCR method used for grafting mouse CDRs to human FRs.

A desired human antibody can be obtained by DNA immunization using a transgenic animal having the complete repertoire of human antibody genes (see International Publication Nos. WO 1993/012227, WO 1992/003918, WO 1994/002602, WO 1994/025585, WO 1996/034096, and WO 1996/033735) as an animal for immunization.

Furthermore, technologies for obtaining a human antibody by panning using a human antibody library are known. For example, a human antibody V region is expressed on the surface of a phage as a single-chain antibody (scFv) by the phage display method. The scFv-expressing phage that binds to the antigen can be selected. The DNA sequence that encodes the V region of the antigen-bound human antibody can be determined by analyzing the genes of the selected phage. After determining the DNA sequence of the scFv that binds to the antigen, an expression vector can be prepared by fusing the V-region sequence in-frame with the sequence of a desired human antibody C region, and then inserting this into a suitable expression vector. The expression vector is introduced into suitable expression cells such as those described above, and the human antibody can be obtained by expressing the human antibody-encoding gene. These methods are already known (see, International Publication Nos. WO 1992/001047, WO 1992/020791, WO 1993/006213, WO 1993/011236, WO 1993/019172, WO 1995/001438, and WO 1995/15388).

Variable regions constituting the antibodies of the present invention can be variable regions that recognize any antigen.

Herein, there is no particular limitation on the antigen, and it may be any antigens. Examples of such antigens preferably include ligands (cytokines, chemokines, and such), receptors, cancer antigens, MHC antigens, differentiation antigens, immunoglobulins, and immune complexes partly containing immunoglobulins.

Examples of cytokines include interleukins 1 to 18 such as IL-6, colony stimulating factors (G-CSF, M-CSF, GM-CSF, etc.), interferons (IFN-α, IFN-β, IFN-γ, etc.), growth factors (EGF, FGF, IGF, NGF, PDGF, TGF, HGF, etc.), tumor necrosis factors (TNF-α and TNF-β), lymphotoxin, erythropoietin, leptin, SCF, TPO, MCAF, and BMP.

Examples of chemokines include CC chemokines such as CCL1 to CCL28, CXC chemokines such as CXCL1 to CXCL17, C chemokines such as XCL1 and XCL2, and CX3C chemokines such as CX3CL1.

Examples of receptors include receptors belonging to receptor families such as the hematopoietic growth factor receptor family, cytokine receptor family, tyrosine kinase-type receptor family, serine/threonine kinase-type receptor family, TNF receptor family, G protein-coupled receptor family, GPI anchor-type receptor family, tyrosine phosphatase-type receptor family, adhesion factor family, and hormone receptor family. The receptors belonging to these receptor families and their characteristics have been described in many documents such as Cooke B A., King R J B., van der Molen H J. ed. New Comprehesive Biochemistry Vol. 18B "Hormones and their Actions Part II" pp. 1-46 (1988) Elsevier Science Publishers B V; Patthy (Cell (1990) 61 (1), 13-14); Ullrich et al. (Cell (1990) 61 (2), 203-212); Massagué (Cell (1992) 69 (6), 1067-1070); Miyajima et al. (Annu. Rev. Immunol. (1992) 10, 295-331); Taga et al. (FASEB J. (1992) 6, 3387-3396); Fantl et al. (Annu. Rev. Biochem. (1993), 62, 453-481); Smith et al. (Cell (1994) 76 (6) 959-962); and Flower D R. Biochim. Biophys. Acta, Flower (Biochim. Biophys. Acta (1999) 1422 (3) 207-234).

Examples of specific receptors belonging to the above-mentioned receptor families preferably include human or mouse erythropoietin (EPO) receptors (Blood (1990) 76 (1), 31-35; and Cell (1989) 57 (2), 277-285), human or mouse granulocyte-colony stimulating factor (G-CSF) receptors (Proc. Natl. Acad. Sci. USA. (1990) 87 (22), 8702-8706, mG-CSFR; Cell (1990) 61 (2), 341-350), human or mouse thrombopoietin (TPO) receptors (Proc Natl Acad Sci USA. (1992) 89 (12), 5640-5644; EMBO J. (1993) 12(7), 2645-53), human or mouse insulin receptors (Nature (1985) 313 (6005), 756-761), human or mouse Flt-3 ligand receptors (Proc. Natl. Acad. Sci. USA. (1994) 91 (2), 459-463), human or mouse platelet-derived growth factor (PDGF) receptors (Proc. Natl. Acad. Sci. USA. (1988) 85 (10) 3435-3439), human or mouse interferon (IFN)-α and β receptors (Cell (1990) 60 (2), 225-234; and Cell (1994) 77 (3), 391-400), human or mouse leptin receptors, human or mouse growth hormone (GH) receptors, human or mouse interleukin (IL)-6 receptors, human or mouse interleukin (IL)-10 receptors, human or mouse insulin-like growth factor (IGF)-I receptors, human or mouse leukemia inhibitory factor (LIF) receptors, human or mouse ciliary neurotrophic factor (CNTF) receptors, and human or mouse chemokine receptors such as CSCR4.

Cancer antigens are antigens that are expressed as cells become malignant, and they are also called tumor-specific antigens. Abnormal sugar chains that appear on cell surfaces or protein molecules when cells become cancerous are also cancer antigens, and they are also called sugar-chain cancer antigens. Examples of cancer antigens preferably include GPC3 which is a receptor belonging to the GPI anchor-type receptor family mentioned above, and is also expressed in several cancers including liver cancer (Int J Cancer. (2003) 103 (4), 455-65), as well as EpCAM which is expressed in several cancers including lung cancer (Proc Natl Acad Sci USA. (1989) 86 (1), 27-31), CA19-9, CA15-3, and sialyl SSEA-1 (SLX).

MHC antigens are roughly classified into MHC class I antigens and MHC class II antigens. MHC class I antigens include HLA-A, -B, -C, -E, -F, -G, and -H, and MHC class II antigens include HLA-DR, -DQ, and -DP.

Differentiation antigens may include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

Immunoglobulins include IgA, IgM, IgD, IgG, and IgE. Immunocomplexes include a component of at least any one of the immunoglobulins.

One or more amino acid residue alterations are allowed in the amino acid sequences constituting the variable regions as long as their antigen-binding activities are maintained. When altering a variable region amino acid sequence, there is no particularly limitation on the site of alteration and number of amino acids altered. For example, amino acids present in CDR and/or FR can be altered appropriately. When altering amino acids in a variable region, the binding activity is preferably maintained without particular limitation; and for example, as compared to before alteration, the binding activity is 50% or more, preferably 80% or more, and more preferably 100% or more. Furthermore, the binding activity may be increased by amino acid alterations. For example, the binding activity may be 2-, 5-, 10-times higher or such than that before alteration. In the antibodies of the present invention, alteration of amino acid sequence may be at least one of amino acid residue substitution, addition, deletion, and modification.

Antibody variable regions of the present invention may have any sequences, and they may be antibody variable regions of any origin, such as mouse antibodies, rat antibodies, rabbit antibodies, goat antibodies, camel antibodies, humanized antibodies produced by humanizing these non-human antibodies, and human antibodies. "Humanized antibodies", also referred to as "reshaped human antibodies", are antibodies in which the complementarity determining regions (CDRs) of an antibody derived from a non-human mammal, for example, a mouse antibody, are transplanted into the CDRs of a human antibody. Methods for identifying CDRs are known (Kabat et al., Sequence of Proteins of Immunological Interest (1987), National Institute of Health, Bethesda, Md.; Chothia et al., Nature (1989) 342: 877). Their common genetic recombination techniques are also known (see, European Patent Application Publication No. EP 125023 and WO 96/02576). Furthermore, these antibodies may have various amino acid substitutions introduced into their variable regions to improve their antigen binding, pharmacokinetics, stability, and antigenicity. Variable regions of the antibodies of the present invention may be able to bind antigens repeatedly due to their pH dependability in antigen binding (WO/2009/125825).

κ chain and λ chain-type constant regions are present in antibody light-chain constant regions, but either one of the light chain constant regions is acceptable. Furthermore, light-chain constant regions of the present invention may be light-chain constant regions with amino acid alterations such as substitutions, deletions, additions, and/or insertions.

Furthermore, the above-mentioned antibody constant regions may be converted into fusion proteins by linking them with various molecules such as bioactive peptides and antigen-binding peptides. Molecules of these bioactive peptides, antigen-binding peptides, and such include, for example, receptors, adhesion molecules, ligands, and enzymes, but are not limited thereto.

Furthermore, antibodies of the present invention include their modified products as long as they are antibodies comprising any one of the above constant regions.

Such antibody modification products include, for example, antibodies linked with various molecules such as polyethylene glycol (PEG) and cytotoxic substances. Such antibody modification products can be obtained by chemically modifying antibodies of the present invention. Methods for modifying antibodies are already established in this field.

The antibodies of the present invention may also be bispecific antibodies. "Bispecific antibody" refers to an antibody that has in a single molecule variable regions that recognize different epitopes. The epitopes may be present in a single molecule or in separate molecules.

The antibody constant regions described above can be used as a constant region in an antibody against an arbitrary antigen. The antigen is not particularly limited.

The antibodies of the present invention can be prepared by methods known to those skilled in the art. For example, methods of substituting other amino acids of interest for one or more amino acid residues or methods of deleting one or more amino acid residues include, for example, site-directed mutagenesis (Hashimoto-Gotoh, T., Mizuno, T., Ogasahara, Y., and Nakagawa, M. An oligodeoxyribonucleotide-directed dual amber method for site-directed mutagenesis. Gene (1995) 152, 271-275; Zoller, M. J., and Smith, M. Oligonucleotide-directed mutagenesis of DNA fragments cloned into M13 vectors. Methods Enzymol. (1983) 100, 468-500; Kramer, W., Drutsa, V., Jansen, H. W., Kramer, B., Pflugfelder, M., and Fritz, H. J. The gapped duplex DNA approach to oligonucleotide-directed mutation construction. Nucleic Acids Res. (1984) 12, 9441-9456; Kramer W., and Fritz H. J. Oligonucleotide-directed construction of mutations via gapped duplex DNA Methods. Enzymol. (1987) 154, 350-367; Kunkel, T. A. Rapid and efficient site-specific mutagenesis without phenotypic selection. Proc. Natl. Acad. Sci. USA (1985) 82, 488-492). These methods can be used to substitute other amino acids of interest for target amino acids in the constant region of an antibody, or delete one or more amino acid residues.

In another embodiment to obtain antibodies, an antibody that binds to an antigen of interest is first prepared by methods known to those skilled in the art. When the prepared antibody is derived from a non-human animal, it can be humanized. The binding activity of the antibody can be determined by known methods. Next, one or more amino acid residues in the constant region of the antibody are deleted or replaced with other amino acids of interest.

The present invention relates to methods for producing an antibody having altered amino acid residues in the heavy-chain constant region, which comprise the steps of:
 (a) expressing a DNA encoding a heavy chain in which one or more amino acid residues in the constant region have been substituted with other amino acids of interest; and
 (b) collecting the expression product of step (a).

Furthermore, the present invention provides polynucleotides encoding heavy-chain constant regions having the amino acid alterations of the present invention, vectors comprising such polynucleotides, host cells carrying such vectors, and methods for producing antibodies, which comprise the step of culturing such host cells.

More specifically, the present invention provides methods for producing a heavy-chain constant region having the amino acid alterations of the present invention, which comprise the steps of:

(a) culturing host cells that comprise a vector introduced with a polynucleotide encoding a heavy-chain constant region having the amino acid alterations of the present invention; and
 (b) obtaining the heavy-chain constant region encoded by the gene.

In the antibody production methods of the present invention, first, a polynucleotide (for example, DNA) encoding an antibody heavy chain in which one or more amino acid residues in the constant region have been substituted with other amino acids of interest, is expressed.

A DNA encoding a heavy chain constant region in which one or more amino acid residues in the constant region are replaced with other amino acids of interest can be prepared, for example, by obtaining a DNA encoding the constant region of a wild-type heavy chain and/or light chain, and introducing an appropriate substitution so that a codon encoding a particular amino acid in the constant region encodes another amino acid of interest.

Alternatively, a DNA encoding a heavy chain in which one or more amino acid residues in the constant region are replaced with other amino acids of interest can also be prepared by designing and then chemically synthesizing a DNA encoding a protein in which one or more amino acid residues in the constant region of the wild type heavy chain are replaced with other amino acids of interest.

The type of amino acid substitution includes the substitutions described herein, but is not limited thereto.

Alternatively, a DNA encoding a heavy chain in which one or more amino acid residues in the constant region are replaced with other amino acids of interest can also be prepared as a combination of partial DNAs. Such combinations of partial DNAs include, for example, the combination of a DNA encoding a variable region and a DNA encoding a constant region, and the combination of a DNA encoding an Fab region and a DNA encoding an Fc region, but are not limited thereto.

Methods for expressing the above-described DNAs include the methods described below. For example, a heavy chain expression vector is constructed by inserting a DNA encoding a heavy chain variable region into an expression vector along with a DNA encoding a heavy chain constant region. Likewise, when preparing an antibody comprising a heavy chain and a light chain, a light chain expression vector is constructed by inserting a DNA encoding a light chain variable region into an expression vector along with a DNA encoding a light chain constant region. Alternatively, these heavy and light chain genes may be inserted into a single vector. Expression vectors include, for example, SV40 virus-based vectors, EB virus-based vectors, and BPV (papilloma virus)-based vectors, but are not limited thereto.

Host cells are co-transformed with an antibody expression vector constructed by the methods described above. Such host cells include the above-described cells such as CHO (Chinese hamster ovary) cells as well as microorganisms such as *E. coli*, yeast, and *Bacillus subtilis*, and plants and animals (Nature Biotechnology (2007) 25, 563-565; Nature Biotechnology (1998) 16, 773-777; Biochemical and Biophysical Research Communications (1999) 255, 444-450; Nature Biotechnology (2005) 23, 1159-1169; Journal of Virology (2001) 75, 2803-2809; Biochemical and Biophysical Research Communications (2003) 308, 94-100). Such host cells also include human embryonic kinder cancer cell-derived HEK298H cells. The transformation can be preferably achieved by using electroporation, the lipofectin method (R. W. Malone et al., Proc. Natl. Acad. Sci. USA (1989) 86, 6077; P. L. Felgner et al., Proc. Natl. Acad. Sci.

USA (1987) 84, 7413), calcium phosphate method (F. L. Graham & A. J. van der Eb, Virology (1973) 52, 456-467), DEAE-Dextran method, and the like.

In the next step of antibody production, the expression products are collected. The expression products can be collected, for example, by culturing the transformants and then separating and purifying the antibodies from the transformed cells or culture media. Separation and purification of antibodies can be achieved by an appropriate combination of methods such as centrifugation, ammonium sulfate fractionation, salting out, ultrafiltration, columns of 1q, FcRn, Protein A, and Protein G, affinity chromatography, ion exchange chromatography, and gel filtration chromatography.

The present invention provides antibodies produced as described above. More specifically, the present invention relates to antibodies that can be produced by the following steps:
(a) expressing in host cells, a DNA encoding an antibody heavy chain which comprises variable and constant regions, and a light chain; and
(b) collecting the antibody expressed in (a).

In the above-mentioned methods, the amino acid sequences of the heavy-chain constant regions are the above-mentioned constant region sequences provided by the present invention.

As described above, the variable regions constituting the antibodies of the present invention can be variable regions that recognize any antigen.

Furthermore, the present invention provides genes which encode antibody constant regions comprising the amino acid alterations of the present invention. The genes encoding the constant regions of the present invention may be any genes such as DNA and RNA.

The present invention also provides vectors carrying the genes. The type of vector can be appropriately selected by those skilled in the art depending on the host cells to be introduced with the vector. For example, the above vectors can be used.

Furthermore, the present invention relates to host cells transformed with the vectors. Host cells can be appropriately selected by those skilled in the art. For example, the above host cells can be used.

The present invention also relates to methods for producing the constant regions of the present invention, which comprise the steps of culturing the host cells and collecting the expressed constant regions of the present invention.

<Methods for Altering the IgG1 Constant Region>

The present invention also relates to methods for reducing the FcγR-binding activity in the human IgG1 constant region of SEQ ID NO: 5 (M112), which comprise the steps of:
(a) substituting another amino acid for Leu at position 234 (EU numbering) in the amino acid sequence of SEQ ID NO: 5 (IgG1 constant region);
(b) substituting another amino acid for Leu at position 235 (EU numbering) in the amino acid sequence of SEQ ID NO: 5 (IgG1 constant region); and
(c) substituting another amino acid for Asn at position 297 (EU numbering) in the amino acid sequence of SEQ ID NO: 5 (IgG1 constant region).

There is no particular limitation on the amino acids after substitution; however, substitutions of Ala for Leu at position 234 (EU numbering), Ala for Leu at position 235 (EU numbering), and Ala for Asn at position 297 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity in the human IgG1 constant region of SEQ ID NO: 5 (M174), which comprise the steps of:
(a) substituting another amino acid for Leu at position 234 (EU numbering) in the amino acid sequence of SEQ ID NO: 5 (IgG1 constant region);
(b) substituting another amino acid for Leu at position 235 (EU numbering) in the amino acid sequence of SEQ ID NO: 5 (IgG1 constant region);
(c) substituting another amino acid for Ala at position 327 (EU numbering) in the amino acid sequence of SEQ ID NO: 5 (IgG1 constant region);
(d) substituting another amino acid for Ala at position 330 (EU numbering) in the amino acid sequence of SEQ ID NO: 5 (IgG1 constant region); and
(e) substituting another amino acid for Pro at position 331 (EU numbering) in the amino acid sequence of SEQ ID NO: 5 (IgG1 constant region).

There is no particular limitation on the amino acids after substitution; however, substitutions of Ala for Leu at position 234 (EU numbering), Ala or Asp for Leu at position 235 (EU numbering), Gly for Ala at position 327 (EU numbering), Ser for Ala at position 330 (EU numbering), and Ser for Pro at position 331 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity in the human IgG1 constant region of SEQ ID NO: 5 (M220), which comprise the steps of:
(a) substituting another amino acid for Leu at position 234 (EU numbering) in the amino acid sequence of SEQ ID NO: 5 (IgG1 constant region);
(b) substituting another amino acid for Leu at position 235 (EU numbering) in the amino acid sequence of SEQ ID NO: 5 (IgG1 constant region);
(c) substituting another amino acid for Asn at position 297 (EU numbering) in the amino acid sequence of SEQ ID NO: 5 (IgG1 constant region);
(d) substituting another amino acid for Ala at position 327 (EU numbering) in the amino acid sequence of SEQ ID NO: 5 (IgG1 constant region);
(e) substituting another amino acid for Ala at position 330 (EU numbering) in the amino acid sequence of SEQ ID NO: 5 (IgG1 constant region); and
(f) substituting another amino acid for Pro at position 331 (EU numbering) in the amino acid sequence of SEQ ID NO: 5 (IgG1 constant region).

There is no particular limitation on the amino acids after substitution; however, substitutions of Ala for Leu at position 234 (EU numbering), Ala for Leu at position 235 (EU numbering), Ala for Asn at position 297 (EU numbering), Gly for Ala at position 327 (EU numbering), Ser for Ala at position 330 (EU numbering), and Ser for Pro at position 331 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity and/or methods for reducing the FcRn-binding activity in the human IgG1 constant region of SEQ ID NO: 5 (M225), which comprise the steps of:

(a) substituting another amino acid for Leu at position 234 (EU numbering) in the amino acid sequence of SEQ ID NO: 5 (IgG1 constant region);
(b) substituting another amino acid for Leu at position 235 (EU numbering) in the amino acid sequence of SEQ ID NO: 5 (IgG1 constant region);
(c) substituting another amino acid for Ala at position 327 (EU numbering) in the amino acid sequence of SEQ ID NO: 5 (IgG1 constant region);
(d) substituting another amino acid for Ala at position 330 (EU numbering) in the amino acid sequence of SEQ ID NO: 5 (IgG1 constant region);
(e) substituting another amino acid for Pro at position 331 (EU numbering) in the amino acid sequence of SEQ ID NO: 5 (IgG1 constant region); and
(f) substituting another amino acid for Asn at position 434 (EU numbering) in the amino acid sequence of SEQ ID NO: 5 (IgG1 constant region).

There is no particular limitation on the amino acids after substitution; however, substitutions of Ala for Leu at position 234 (EU numbering), Ala for Leu at position 235 (EU numbering), Gly for Ala at position 327 (EU numbering), Ser for Ala at position 330 (EU numbering), Ser for Pro at position 331 (EU numbering), and Ala for Asn at position 434 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity in the human IgG1 constant region of SEQ ID NO: 5 (M226), which comprise the steps of:
(a) substituting another amino acid for Leu at position 234 (EU numbering) in the amino acid sequence of SEQ ID NO: 5 (IgG1 constant region);
(b) substituting another amino acid for Leu at position 235 (EU numbering) in the amino acid sequence of SEQ ID NO: 5 (IgG1 constant region);
(c) substituting another amino acid for Ala at position 327 (EU numbering) in the amino acid sequence of SEQ ID NO: 5 (IgG1 constant region);
(d) substituting another amino acid for Ala at position 330 (EU numbering) in the amino acid sequence of SEQ ID NO: 5 (IgG1 constant region);
(e) substituting another amino acid for Pro at position 331 (EU numbering) in the amino acid sequence of SEQ ID NO: 5 (IgG1 constant region);
(f) substituting another amino acid for His at position 268 (EU numbering) in the amino acid sequence of SEQ ID NO: 5 (IgG1 constant region);
(g) substituting another amino acid for Lys at position 274 (EU numbering) in the amino acid sequence of SEQ ID NO: 5 (IgG1 constant region);
(h) substituting another amino acid for Arg at position 355 (EU numbering) in the amino acid sequence of SEQ ID NO: 5 (IgG1 constant region);
(i) substituting another amino acid for Asp at position 356 (EU numbering) in the amino acid sequence of SEQ ID NO: 5 (IgG1 constant region);
(j) substituting another amino acid for Leu at position 358 (EU numbering) in the amino acid sequence of SEQ ID NO: 5 (IgG1 constant region); and
(k) substituting another amino acid for Gln at position 419 (EU numbering) in the amino acid sequence of SEQ ID NO: 5 (IgG1 constant region).

There is no particular limitation on the amino acids after substitution; however, substitutions of Ala for Leu at position 234 (EU numbering), Ala for Leu at position 235 (EU numbering), Gly for Ala at position 327 (EU numbering), Ser for Ala at position 330 (EU numbering), Ser for Pro at position 331 (EU numbering), Gln for His at position 268 (EU numbering), Gln for Lys at position 274 (EU numbering), Gln for Arg at position 355 (EU numbering), Glu for Asp at position 356 (EU numbering), Met for Leu at position 358 (EU numbering), and Glu for Gln at position 419 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity in the human IgG1/IgG4 constant region of SEQ ID NO: 8 (M228), which comprise the steps of:
(a) substituting another amino acid for Phe at position 234 (EU numbering) in the amino acid sequence of SEQ ID NO: 8 (a constant region having CH1 and Hinge of IgG1, and CH2 and CH3 of IgG4, i.e., IgG1/IgG4 constant region);
(b) substituting another amino acid for Leu at position 235 (EU numbering) in the amino acid sequence of SEQ ID NO: 8 (a constant region having CH1 and Hinge of IgG1, and CH2 and CH3 of IgG4, i.e., IgG1/IgG4 constant region); and
(c) substituting another amino acid for Arg at position 409 (EU numbering) in the amino acid sequence of SEQ ID NO: 8 (a constant region having CH1 and Hinge of IgG1, and CH2 and CH3 of IgG4, i.e., IgG1/IgG4 constant region).

There is no particular limitation on the amino acids after substitution; however, substitutions of Ala for Leu at position 234 (EU numbering), Ala for Leu at position 235 (EU numbering), and Lys for Arg at position 409 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity in the human IgG2 constant region of SEQ ID NO: 6 (M86), which comprise the steps of:
(a) substituting another amino acid for Asn at position 297 (EU numbering) in the amino acid sequence of SEQ ID NO: 6 (IgG2 constant region).

There is no particular limitation on the amino acids after substitution; however, substitution of Ala for Asn at position 297 (EU numbering) is preferred.

As long as the above-mentioned step is included, the methods of the present invention may comprise other amino acid alterations (substitutions, deletions, additions, and/or insertions) or modifications, or other steps.

The present invention also relates to methods for reducing the FcγR-binding activity in the human IgG2 constant region of SEQ ID NO: 6 (M221), which comprise the steps of:
(a) substituting another amino acid for Val at position 234 (EU numbering) in the amino acid sequence of SEQ ID NO: 6 (IgG2 constant region);
(b) substituting another amino acid for Gly at position 237 (EU numbering) in the amino acid sequence of SEQ ID NO: 6 (IgG2 constant region); and
(c) substituting another amino acid for Asn at position 297 (EU numbering) in the amino acid sequence of SEQ ID NO: 6 (IgG2 constant region).

There is no particular limitation on the amino acids after substitution; however, substitutions of Ala for Val at position 234 (EU numbering), Ala for Gly at position 237 (EU numbering), and Ala for Asn at position 297 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity in the human IgG2 constant region of SEQ ID NO: 6 (M222), which comprise the steps of:
(a) substituting another amino acid for Ala at position 330 (EU numbering) in the amino acid sequence of SEQ ID NO: 6 (IgG2 constant region);
(b) substituting another amino acid for Pro at position 331 (EU numbering) in the amino acid sequence of SEQ ID NO: 6 (IgG2 constant region); and
(c) substituting another amino acid for Thr at position 339 (EU numbering) in the amino acid sequence of SEQ ID NO: 6 (IgG2 constant region).

There is no particular limitation on the amino acids after substitution; however, substitutions of Ser for Ala at position 330 (EU numbering), Ser for Pro at position 331 (EU numbering); and Ala for Thr at position 339 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity in the human IgG2 constant region of SEQ ID NO: 6 (M223), which comprise the steps of:
(a) substituting another amino acid for Val at position 234 (EU numbering) in the amino acid sequence of SEQ ID NO: 6 (IgG2 constant region);
(b) substituting another amino acid for Gly at position 237 (EU numbering) in the amino acid sequence of SEQ ID NO: 6 (IgG2 constant region);
(c) substituting another amino acid for Ala at position 330 (EU numbering) in the amino acid sequence of SEQ ID NO: 6 (IgG2 constant region);
(d) substituting another amino acid for Pro at position 331 (EU numbering) in the amino acid sequence of SEQ ID NO: 6 (IgG2 constant region); and
(e) substituting another amino acid for Thr at position 339 (EU numbering) in the amino acid sequence of SEQ ID NO: 6 (IgG2 constant region).

There is no particular limitation on the amino acids after substitution; however, substitutions of Ala for Val at position 234 (EU numbering), Ala for Gly at position 237 (EU numbering), Ser for Ala at position 330 (EU numbering), Ser for Pro at position 331 (EU numbering), and Ala for Thr at position 339 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity in the human IgG2 constant region of SEQ ID NO: 6 (M224), which comprise the steps of:
(a) substituting another amino acid for Val at position 234 (EU numbering) in the amino acid sequence of SEQ ID NO: 6 (IgG2 constant region);
(b) substituting another amino acid for Gly at position 237 (EU numbering) in the amino acid sequence of SEQ ID NO: 6 (IgG2 constant region);
(c) substituting another amino acid for Asn at position 297 (EU numbering) in the amino acid sequence of SEQ ID NO: 6 (IgG2 constant region);
(d) substituting another amino acid for Ala at position 330 (EU numbering) in the amino acid sequence of SEQ ID NO: 6 (IgG2 constant region);
(e) substituting another amino acid for Pro at position 331 (EU numbering) in the amino acid sequence of SEQ ID NO: 6 (IgG2 constant region); and
(f) substituting another amino acid for Thr at position 339 (EU numbering) in the amino acid sequence of SEQ ID NO: 6 (IgG2 constant region).

There is no particular limitation on the amino acids after substitution; however, substitutions of Ala for Val at position 234 (EU numbering), Ala for Gly at position 237 (EU numbering), Ala for Asn at position 297 (EU numbering), Ser for Ala at position 330 (EU numbering), Ser for Pro at position 331 (EU numbering), and Ala for Thr at position 339 (EU numbering) are preferred.

As long as the above-mentioned steps are included, the methods of the present invention may comprise other amino acid alterations (substitutions, deletions, additions, and/or insertions) or modifications, or other steps.

The present invention also relates to methods for reducing the FcγR-binding activity, methods for lowering the isoelectric point, and/or methods for increasing the FcRn-binding activity in the human IgG2 constant region of SEQ ID NO: 6 (M211), which comprise the steps of:
(a) substituting another amino acid for His at position 268 (EU numbering) in the amino acid sequence of SEQ ID NO: 6 (IgG2 constant region);
(b) substituting another amino acid for Arg at position 355 (EU numbering) in the amino acid sequence of SEQ ID NO: 6 (IgG2 constant region);
(c) substituting another amino acid for Gln at position 419 (EU numbering) in the amino acid sequence of SEQ ID NO: 6 (IgG2 constant region); and
(d) substituting another amino acid for Asn at position 434 (EU numbering) in the amino acid sequence of SEQ ID NO: 6 (IgG2 constant region).

There is no particular limitation on the amino acids after substitution; however, substitutions of Gln for His at position 268 (EU numbering), Gln for Arg at position 355 (EU numbering), Glu for Gln at position 419 (EU numbering), and Ala for Asn at position 434 (EU numbering) are preferred.

As long as the above-mentioned steps are included, the methods of the present invention may comprise other amino acid alterations (substitutions, deletions, additions, and/or insertions) or modifications, or other steps.

With regard to the human IgG2 constant region of SEQ ID NO: 6 (M209), the present invention relates to methods for reducing its FcγR-binding activity, methods for lowering its isoelectric point, methods for increasing its FcRn-binding activity, and/or methods for decreasing its heterogeneity, which comprise the steps of:
(a) substituting another amino acid for His at position 268 (EU numbering) in the amino acid sequence of SEQ ID NO: 6 (IgG2 constant region);
(b) substituting another amino acid for Arg at position 355 (EU numbering) in the amino acid sequence of SEQ ID NO: 6 (IgG2 constant region);
(c) substituting another amino acid for Gln at position 419 (EU numbering) in the amino acid sequence of SEQ ID NO: 6 (IgG2 constant region);

(d) substituting another amino acid for Asn at position 434 (EU numbering) in the amino acid sequence of SEQ ID NO: 6 (IgG2 constant region);
(e) substituting another amino acid for Cys at position 131 (EU numbering) in the amino acid sequence of SEQ ID NO: 6 (IgG2 constant region);
(f) substituting another amino acid for Arg at position 133 (EU numbering) in the amino acid sequence of SEQ ID NO: 6 (IgG2 constant region);
(g) substituting another amino acid for Glu at position 137 (EU numbering) in the amino acid sequence of SEQ ID NO: 6 (IgG2 constant region);
(h) substituting another amino acid for Ser at position 138 (EU numbering) in the amino acid sequence of SEQ ID NO: 6 (IgG2 constant region); and
(i) substituting another amino acid for Cys at position 220 (EU numbering) in the amino acid sequence of SEQ ID NO: 6 (IgG2 constant region).

There is no particular limitation on the amino acids after substitution; however, substitutions of Gln for His at position 268 (EU numbering), Gln for Arg at position 355 (EU numbering), Glu for Gln at position 419 (EU numbering), Ala for Asn at position 434 (EU numbering), Ser for Cys at position 131 (EU numbering), Lys for Arg at position 133 (EU numbering), Gly for Glu at position 137 (EU numbering), Gly for Ser at position 138 (EU numbering), and Ser for Cys at position 220 (EU numbering) are preferred.

Step (i) above may be a step that substitutes another amino acid for Cys at position 219 (EU numbering) in the amino acid sequence of SEQ ID NO: 6 (IgG2 constant region), instead of substituting another amino acid for Cys at position 220 (EU numbering) in the amino acid sequence of SEQ ID NO: 6 (IgG2 constant region). In this case, Ser substitution for Cys at position 219 (EU numbering) is preferred.

As long as the above-mentioned steps are included, the methods of the present invention may comprise other amino acid alterations (substitutions, deletions, additions, and/or insertions) or modifications, or other steps.

<Pharmaceutical Compositions Comprising Antibodies>

The present invention provides pharmaceutical compositions comprising an antibody or a constant region of the present invention.

The pharmaceutical compositions of the present invention can be formulated, in addition to the antibody or constant region, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as POLYSORBATE 80™ (polyoxyethylene (20) sorbitan monooleate) surfactant and HCO-50 (polyethylene glycol (PEG)-50 hydrogenated castor oil) surfactant.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dosage of the pharmaceutical composition containing an antibody or a polynucleotide encoding an antibody can be selected, for example, from the range of 0.0001 to 1,000 mg per kg of body weight. Alternatively, the dosage may be, for example, in the range of 0.001 to 100,000 mg/patient. However, the dosage is not limited to these values. The dosage and method of administration vary depending on the patient's body weight, age, and symptoms, and can be appropriately selected by those skilled in the art.

Correspondence between amino acid positions according to EU numbering and amino acid positions in the amino acid sequences described in the sequence listing is as shown below.

Leu at position 234, EU numbering, in the amino acid sequence of SEQ ID NO: 5 (IgG1 constant region): Leu at position 117 in SEQ ID NO: 5 (IgG1 constant region);

Leu at position 235, EU numbering, in the amino acid sequence of SEQ ID NO: 5 (IgG1 constant region): Leu at position 118 in SEQ ID NO: 5 (IgG1 constant region);

Asn at position 297, EU numbering, in the amino acid sequence of SEQ ID NO: 5 (IgG1 constant region): Asn at position 180 in SEQ ID NO: 5 (IgG1 constant region);

Ala at position 327, EU numbering, in the amino acid sequence of SEQ ID NO: 5 (IgG1 constant region): Ala at position 210 in SEQ ID NO: 5 (IgG1 constant region);

Ala at position 330, EU numbering, in the amino acid sequence of SEQ ID NO: 5 (IgG1 constant region): Ala at position 213 in SEQ ID NO: 5 (IgG1 constant region);

Pro at position 331, EU numbering, in the amino acid sequence of SEQ ID NO: 5 (IgG1 constant region): Pro at position 214 in SEQ ID NO: 5 (IgG1 constant region);

Asn at position 434, EU numbering, in the amino acid sequence of SEQ ID NO: 5 (IgG1 constant region): Asn at position 317 in SEQ ID NO: 5 (IgG1 constant region);

His at position 268, EU numbering, in the amino acid sequence of SEQ ID NO: 5 (IgG1 constant region): His at position 151 in SEQ ID NO: 5 (IgG1 constant region);

Lys at position 274, EU numbering, in the amino acid sequence of SEQ ID NO: 5 (IgG1 constant region): Lys at position 157 in SEQ ID NO: 5 (IgG1 constant region);

Arg at position 355, EU numbering, in the amino acid sequence of SEQ ID NO: 5 (IgG1 constant region): Arg at position 238 in SEQ ID NO: 5 (IgG1 constant region);

Asp at position 356, EU numbering, in the amino acid sequence of SEQ ID NO: 5 (IgG1 constant region): Asp at position 239 in SEQ ID NO: 5 (IgG1 constant region);

Leu at position 358, EU numbering, in the amino acid sequence of SEQ ID NO: 5 (IgG1 constant region): Leu at position 241 in SEQ ID NO: 5 (IgG1 constant region);

Gln at position 419, EU numbering, in the amino acid sequence of SEQ ID NO: 5 (IgG1 constant region): Gln at position 302 in SEQ ID NO: 5 (IgG1 constant region);

Phe at position 234, EU numbering, in the amino acid sequence of SEQ ID NO: 8 (a constant region having CH1 and Hinge of IgG1, and CH2 and CH3 of IgG4, i.e., IgG1/IgG4 constant region): Phe at position 117 in SEQ ID NO: 8 (IgG1/IgG4 constant region);

Leu at position 235, EU numbering, in the amino acid sequence of SEQ ID NO: 8 (a constant region having CH1 and Hinge of IgG1, and CH2 and CH3 of IgG4, i.e., IgG1/IgG4 constant region): Leu at position 118 in SEQ ID NO: 8 (IgG1/IgG4 constant region);

Arg at position 409, EU numbering, in the amino acid sequence of SEQ ID NO: 8 (a constant region having CH1 and Hinge of IgG1, and CH2 and CH3 of IgG4, i.e., IgG1/IgG4 constant region): Arg at position 292 in SEQ ID NO: 8 (IgG1/IgG4 constant region);

Asn at position 297, EU numbering, in the amino acid sequence of SEQ ID NO: 6 (IgG2 constant region): Asn at position 176 in SEQ ID NO: 6 (IgG2 constant region);

Val at position 234, EU numbering, in the amino acid sequence of SEQ ID NO: 6 (IgG2 constant region): Val at position 114 in SEQ ID NO: 6 (IgG2 constant region);

Gly at position 237, EU numbering, in the amino acid sequence of SEQ ID NO: 6 (IgG2 constant region): Gly at position 116 in SEQ ID NO: 6 (IgG2 constant region);

Ala at position 330, EU numbering, in the amino acid sequence of SEQ ID NO: 6 (IgG2 constant region): Ala at position 209 in SEQ ID NO: 6 (IgG2 constant region);

Pro at position 331, EU numbering, in the amino acid sequence of SEQ ID NO: 6 (IgG2 constant region): Pro at position 210 in SEQ ID NO: 6 (IgG2 constant region);

His at position 268, EU numbering, in the amino acid sequence of SEQ ID NO: 6 (IgG2 constant region): His at position 147 in SEQ ID NO: 6 (IgG2 constant region);

Arg at position 355, EU numbering, in the amino acid sequence of SEQ ID NO: 6 (IgG2 constant region): Arg at position 234 in SEQ ID NO: 6 (IgG2 constant region);

Gln at position 419, EU numbering, in the amino acid sequence of SEQ ID NO: 6 (IgG2 constant region): Gln at position 298 in SEQ ID NO: 6 (IgG2 constant region);

Asn at position 434, EU numbering, in the amino acid sequence of SEQ ID NO: 6 (IgG2 constant region): Asn at position 313 in SEQ ID NO: 6 (IgG2 constant region);

Cys at position 131, EU numbering, in the amino acid sequence of SEQ ID NO: 6 (IgG2 constant region): Cys at position 14 in SEQ ID NO: 6 (IgG2 constant region);

Arg at position 133, EU numbering, in the amino acid sequence of SEQ ID NO: 6 (IgG2 constant region): Arg at position 16 in SEQ ID NO: 6 (IgG2 constant region);

Glu at position 137, EU numbering, in the amino acid sequence of SEQ ID NO: 6 (IgG2 constant region): Glu at position 20 in SEQ ID NO: 6 (IgG2 constant region);

Ser at position 138, EU numbering, in the amino acid sequence of SEQ ID NO: 6 (IgG2 constant region): Ser at position 21 in SEQ ID NO: 6 (IgG2 constant region);

Cys at position 220, EU numbering, in the amino acid sequence of SEQ ID NO: 6 (IgG2 constant region): Cys at position 103 in SEQ ID NO: 6 (IgG2 constant region); and Thr at position 339, EU numbering, in the amino acid sequence of SEQ ID NO: 6 (IgG2 constant region): Thr at position 218 in SEQ ID NO: 6 (IgG2 constant region).

As used herein, the three-letter and single-letter codes for respective amino acids are as follows:

Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

All prior art documents cited herein are incorporated by reference in their entirety.

EXAMPLES

Herein below, the present invention will be specifically described further with reference to the Examples, but it is not to be construed as being limited thereto. In the Examples, altered amino acid sites in the constant region are indicated using the EU numbering system (see, Sequences of proteins of immunological interest, NIH Publication No. 91-3242).

Example 1

Evaluation of the Binding of Constant Regions IgG1, 2, and 4 to FcγR

In this Example, first, an antibody was generated based on the amino acid sequence of an anti-IL-6 receptor antibody (Tocilizumab; brand name: Actemra; antibody class: IgG1). The antibody has a sequence in which the C-terminal amino acid sequence GK has been removed from its constant region. Specifically, H0-G1d/L0-k0 comprising H0-G1d (SEQ ID NO: 31) as the H chain and L0-k0 (SEQ ID NO: 32) as the L chain was produced. As antibodies with different constant regions, H0-G2d/L0-k0 comprising H0-G2d (Acid SEQ ID NO: 33) as the H chain and L0-k0 (SEQ ID NO: 32) as the L chain, and H0-G4d/L0-k0 comprising H0-G4d (Acid SEQ ID NO: 34) as the H chain and L0-k0 (Acid SEQ ID NO: 32) as the L chain were produced. Expression and purification of the antibodies were carried out by the method described in Reference Example 1

Using the prepared antibodies, affinity towards the Fcγ receptor (FcγR) was measured by the method described in Reference Example 2. The results are shown in FIG. 1.

The binding of each subclass towards FcγR closely correlates with the reported order (References 6 and 7).

Example 2

Production and Evaluation of IgG1 Constant Regions that Reduce FcγR Binding

Anti-CD3 antibodies have been reported to induce cytokine release (References 1 and 2). One of the reasons may be that association of the constant region with FcγR activates cells and leads to cytokine release. To reduce the cytokine release caused by anti-CD3 antibody administration, clinical studies are being conducted on anti-CD3 antibodies having a constant region that shows reduced binding of the constant region to FcγR (References 1 and 2).

Anti-CD3 antibodies having a constant region with reduced binding to FcγR are Otelixizumab and Teplizumab. The constant region of Otelixizumab has N297A (hereinafter, described as Agly) alteration and the constant region of Teplizumab has L234A and L235A (hereinafter, described as LALA) alterations. These alterations are known to reduce binding to FcγR. Therefore, constant regions introduced with these alterations, M111 (SEQ ID NO: 10) and M119 (SEQ ID NO: 12) were produced. Antibodies having a variable region used in Example 1 and the produced constant region were generated, and each antibody was prepared by the method described in Reference Example 1.

Comparison of the constant regions of G1 and G4 shows that amino acids at positions 327, 330, and 331 are different, and these amino acids are important for ADCC (Reference 3). Therefore, a constant region introduced with these alterations, M16 (SEQ ID NO: 9), was produced. Antibodies having a variable region used in Example 1 and the produced constant region were constructed, and each antibody was prepared by the method described in Reference Example 1.

Figure 2:
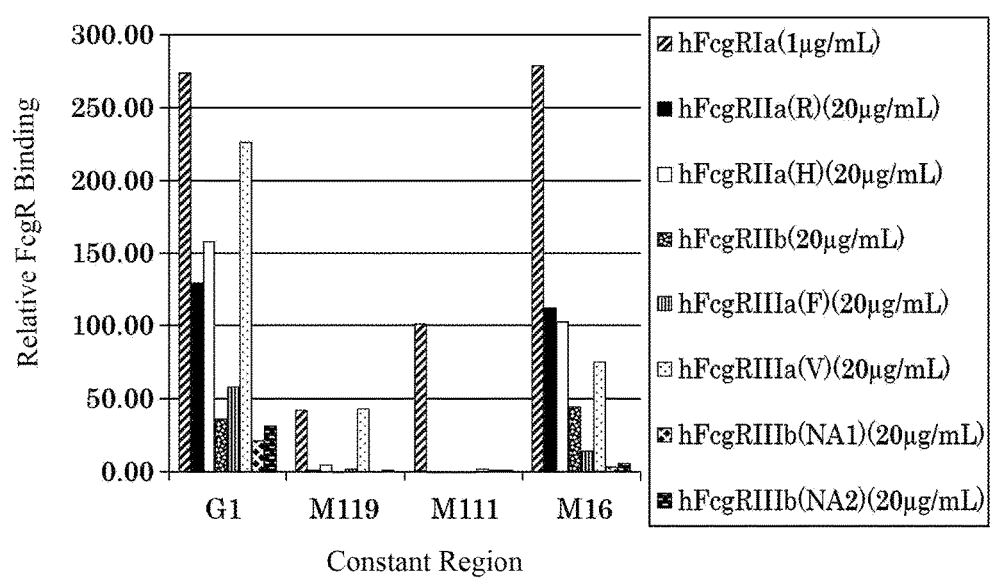
FIG. 2 shows comparison of the amount of FcγR binding by M111, M119, and M16.

Using the prepared antibodies, affinity towards FcγR was measured by the method described in Reference Example 2. The results are shown in FIG. 2.

As a result, M111 bound to FcγI, M119 bound to FcγI and FcγIII, and M16 bound to almost all FcγRs. Therefore, this showed that none of the constant regions produced completely lost its binding to FcγR.

Example 3

Figure 3:
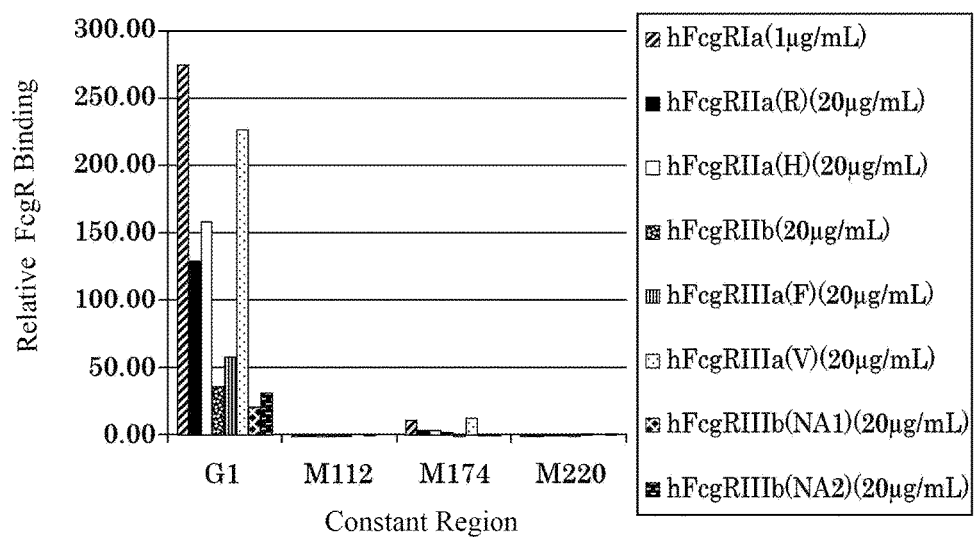
FIG. 3 shows comparison of the amount of FcγR binding by M112, M174, and M220.

Production and Evaluation of Novel IgG1 Constant Regions that Reduce FcγR Binding To produce constant regions that have completely eliminated their binding to FcγR, M112 (SEQ ID NO: 11), M174 (SEQ ID NO: 13), and M220 (SEQ ID NO: 14) which contain combinations of the above-mentioned alterations were produced. Antibodies having a variable region used in Example 1 and the produced constant region were constructed, and each antibody was prepared by the method described in Reference Example 1. Using the prepared antibodies, affinity towards FcγR was measured by the method described in Reference Example 2. The results are shown in FIG. 3.

The results showed that FcγR binding was greatly reduced in all of the constant regions, M112, M174, and M220.

TABLE 1

|  | 234 | 235 | 297 | 327 | 330 | 331 |
|---|---|---|---|---|---|---|
| IgG1 | L | L | N | A | A | P |
| IgG2 | V | A | N | G | A | P |
| IgG4 | F | L | N | G | S | S |
| IgG1 based | | | | | | |
| M111 | L | L | A | A | A | P |
| M119 | A | A | N | A | A | P |
| M16 | L | L | N | G | S | S |
| M112 | A | A | A | A | A | P |
| M174 | A | A | N | G | S | S |
| M220 | A | A | A | G | S | S |

Example 4

Effect of Optimization of the Novel Constant Regions on Binding to FcγR

Figure 4:
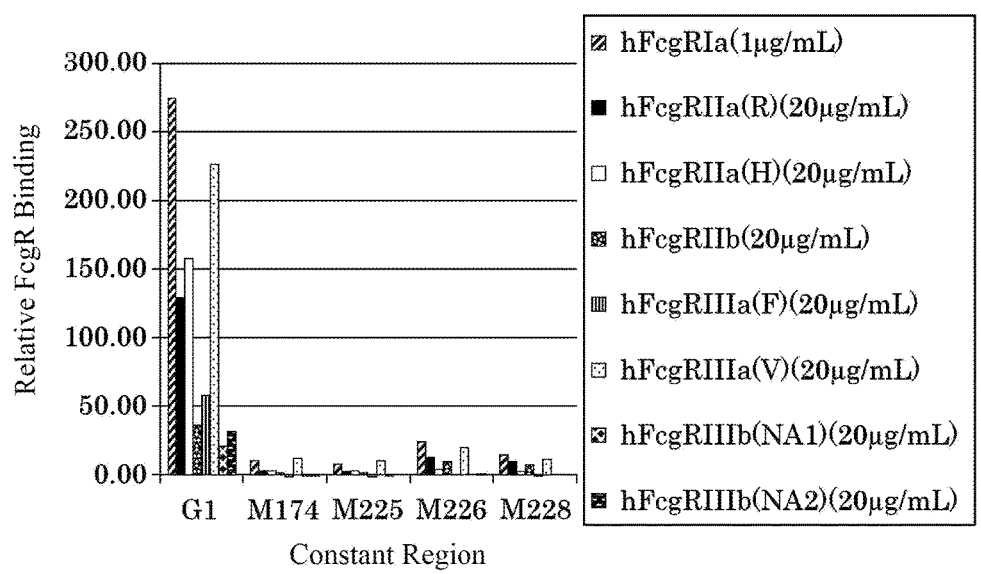
FIG. 4 shows comparison of the amount of FcγR binding by M225, M226, and M228.

Various optimizations of constant regions have been carried out to further enhance the long half-life characteristic of antibodies. One of them was to optimize for the improvement of binding with FcRn (Reference Document 4). Furthermore, it has been reported that the half-life of antibody in blood is improved by reducing the isoelectric point (Reference Document 5). Therefore, M225 (SEQ ID NO: 15) was prepared by introducing into M174 the N434A alteration which improves half-life, and M226 (SEQ ID NO: 16) was prepared by adding alterations that decrease the pI of the constant region to M174. To reduce the FcγR binding in M226, the sequence of positions 327, 330, and 331 was substituted from G1 to G4; and to reduce the pI, part of the sequence was substituted from the G1 sequence to the G4 sequence. Then, M228 (SEQ ID NO: 17) was generated by converting the amino acids downstream of position 237 to G4, and adding the R409K alteration to improve acid stability. Antibodies having a variable region used in Example 1 and the produced constant region were generated, and each antibody was prepared by the method described in Reference Example 1. Using the prepared antibodies, affinity to FcγR was measured by the method described in Reference Example 2. The results are shown in FIG. 4.

The results showed that FcγR binding was lower in any of the constant regions than in IgG1.

Example 5

Figure 5:
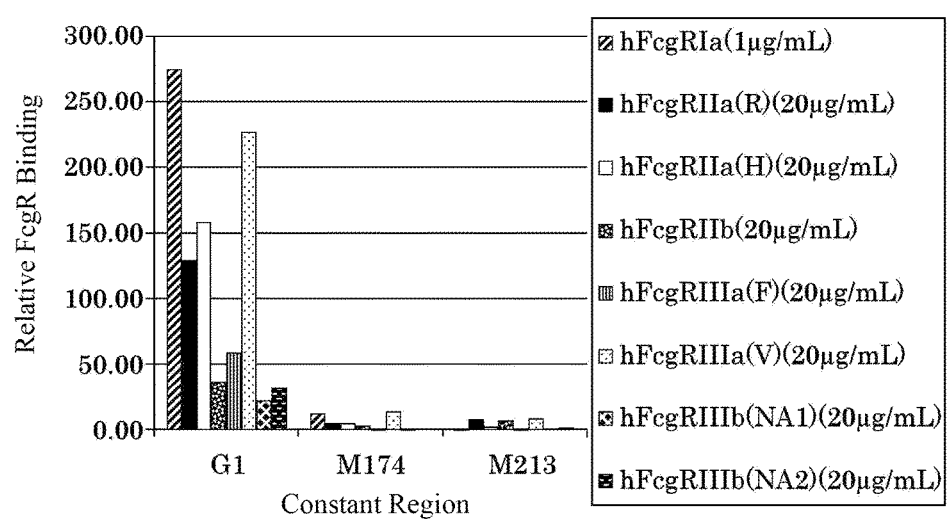
FIG. 5 shows comparison of the amount of FcγR binding by M174 and M213.

Production and Evaluation of Novel IgG1 Constant Regions that Reduce Binding to FcγR Compared to M112 and M220, M174 slightly binds to each FcγR, and therefore, further optimizations were carried out. M213 (SEQ ID NO: 18) which contains the L235D alteration was produced. Antibodies having a variable region used in Example 1 and the produced constant region were constructed, and each antibody was prepared by the method described in Reference Example 1. Using the prepared antibodies, affinity towards FcγR was measured by the method described in Reference Example 2. The results are shown in FIG. 5. The results showed that FcγR binding was reduced in M213 compared to M174.

TABLE 2

|      | 234 | 235 | 297 | 327 | 330 | 331 |
|------|-----|-----|-----|-----|-----|-----|
| IgG1 | L   | L   | N   | A   | A   | P   |
| IgG2 | V   | A   | N   | G   | A   | P   |
| IgG4 | F   | L   | N   | G   | S   | S   |
| IgG1 based | | | | | | |
| M174 | A   | A   | N   | G   | S   | S   |
| M213 | A   | D   | N   | G   | S   | S   |

Example 6

Production and Evaluation of IgG2 Constant Regions that Reduce Binding to FcγR

Figure 6:
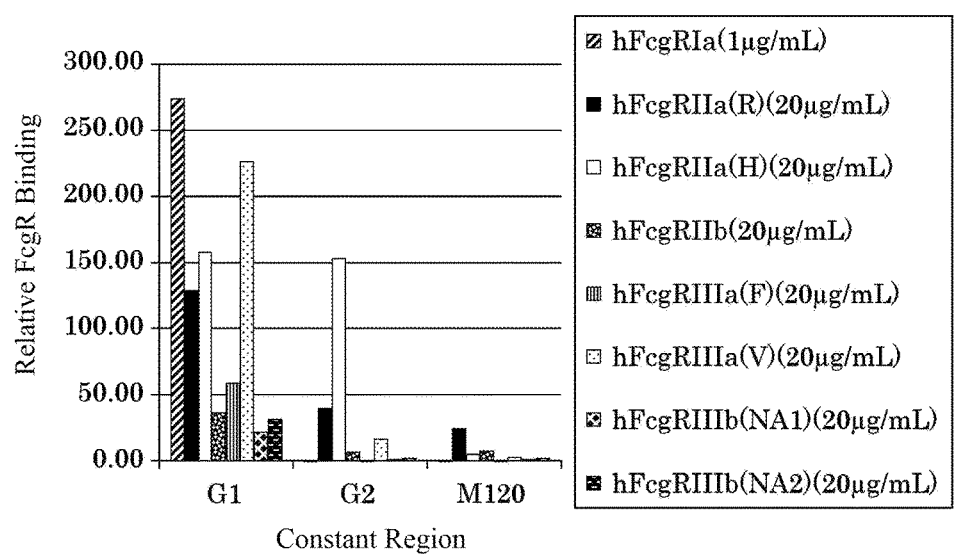
FIG. 6 shows comparison of the amount of FcγR binding by wt-IgG2 and M120.

As described in Example 1, antibodies against CD3 have been reported to induce cytokine release (References 1 and 2). Visilizumab was produced by optimizing IgG2 to reduce binding of the constant region to FcγR (References 1 and 2). V234A and G237A alterations were carried out in Visilizumab. Therefore, M120 (SEQ ID NO: 19) which has these IgG2 alterations performed was produced. Antibodies having a variable region used in Example 1 and the produced constant region were generated, and each antibody was prepared by the method described in Reference Example 1. Using the prepared antibodies, affinity towards FcγR was measured by the method described in Reference Example 2. The results are shown in FIG. 6.

This revealed that compared to M120, IgG2 has a decreased affinity towards FcγR, but it is not completely lost.

TABLE 3

|      | 234 | 235 | 236 | 237 | 297 | 327 | 330 | 331 |
|------|-----|-----|-----|-----|-----|-----|-----|-----|
| IgG1 | L   | L   | G   | G   | N   | A   | A   | P   |
| IgG2 | V   | A   |     | G   | N   | G   | A   | P   |
| IgG4 | F   | L   | G   | G   | N   | G   | S   | S   |
| IgG1 based | | | | | | | | |
| M120 | A   | A   |     | A   | N   | G   | A   | P   |

Example 7

Figure 7:
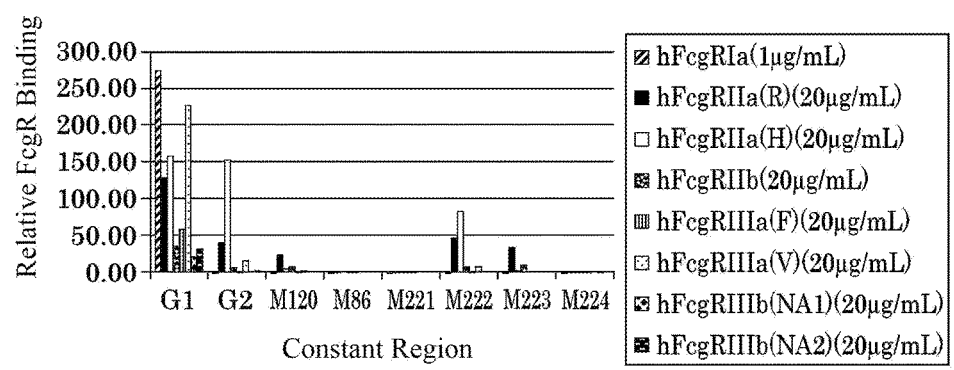
FIG. 7 shows comparison of the amount of FcγR binding by M86, M221, M222, M223, and M224.

Production and Evaluation of Novel IgG2 Constant Regions that Reduce Binding to FcγR To completely remove binding of the IgG2 constant region to various types of FcγR, M86 (SEQ ID NO: 20), M221 (SEQ ID NO: 21), M222 (SEQ ID NO: 22), M223 (SEQ ID NO: 23), and M224 (SEQ ID NO: 24) were produced. Antibodies having a variable region used in Example 1 and the produced constant region were generated, and each antibody was prepared by the method described in Reference Example 1. The affinity towards FcγR was measured by the method described in Reference Example 2 using the prepared antibodies. The results are shown in FIG. 7.

The results showed that FcγR binding was lower in any of the constant regions than in IgG2.

TABLE 4

|      | 234 | 235 | 236 | 237 | 297 | 327 | 330 | 331 | 339 |
|------|-----|-----|-----|-----|-----|-----|-----|-----|-----|
| IgG1 | L   | L   | G   | G   | N   | A   | A   | P   | A   |
| IgG2 | V   | A   |     | G   | N   | G   | A   | P   | T   |
| IgG4 | F   | L   | G   | G   | N   | G   | S   | S   | A   |
| IgG2 based | | | | | | | | | |
| M120 | A   | A   |     | A   | N   | G   | A   | P   | T   |
| M86  | V   | A   |     | G   | A   | G   | A   | P   | T   |
| M221 | A   | A   |     | A   | A   | G   | A   | P   | T   |
| M222 | V   | A   |     | G   | N   | G   | S   | S   | A   |
| M223 | A   | A   |     | A   | N   | G   | S   | S   | A   |
| M224 | A   | A   |     | A   | A   | G   | S   | S   | A   |

Example 8

Effect of Optimizing the Novel Constant Regions on Binding to FcγR

Figure 8:
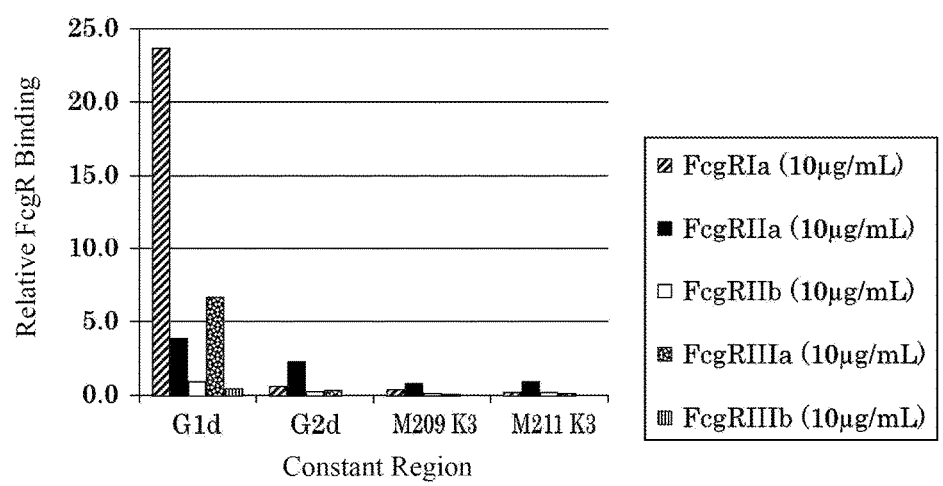
FIG. 8 shows comparison of the amount of FcγR binding by M209 and M211.

To improve the half-life of M120, M211 (SEQ ID NO: 25) was produced with a constant region having lower isoelectric point and enhanced binding to FcRn. To decrease the heterogeneous components of IgG2, Cys was modified in M211 to produce M209 (SEQ ID NO: 26). The produced constant regions were combined with k3 which has a shortened L chain length to produce M211/k3 and M209/k3. Each antibody was prepared by the method described in Reference Example 1. Using the prepared antibodies, affinity towards FcγR was measured by the method described in Reference Example 2. The results are shown in FIG. 8.

The results showed that when compared to IgG2, M209 and M211 have reduced binding to FcγR.

Example 9

Effects of Novel Constant Regions on FcγR Binding

Antibodies were constructed by connecting an IgG1, IgG2, or IgG4 constant region with an anti-human CXCR4 antibody. The IgG1 constant region was modified with the above alterations. Specifically, anti-CXCR4 antibodies with modified constant regions were bound by the above-mentioned constant region, M119, M111, M112, M16, M174, or M220, and the affinity of the constructed antibodies towards FcγR was measured by the method described in Reference Example 2.

The results showed that M112 and M220 completely lost affinity to all FcγRs, and when compared to IgG1, M174 had a dramatically reduced affinity towards FcgR.

Reference Example 1

Construction of Antibody Expression Vectors; and Expression and Purification of Antibodies Synthesis of full-length genes encoding the nucleotide sequences of the H chain and L chain of the antibody variable regions was carried out by production methods known to those skilled in the art using Assemble PCR and such. Introduction of amino acid substitutions was carried out by methods known to those skilled in the art using the QuikChange Site-Directed Mutagenesis Kit (Stratagene), PCR, or such. The obtained plasmid fragment was inserted into an animal cell expression vector, and the H-chain expression vector and L-chain expression vector were produced. The nucleotide sequence of the obtained expression vector was determined by methods known to those skilled in the art. The produced plasmids were introduced transiently into the HEK293 cell line derived from human embryonic kidney cancer cells (Invitrogen) or into Free Style293 cells (Invitrogen) for antibody expression. The obtained culture supernatant was collected, and then passed through a 0.22 μm filter or MILLEX(R)-GV filter (Millipore), or through a 0.45 μm MILLEX(R)-GV filter (Millipore) to obtain the culture supernatant. Antibodies were purified from the obtained culture supernatant by methods known to those skilled in the art using rProtein A Sepharose TM Fast Flow column chromatography (GE Healthcare). For the concentration of the purified antibodies, their absorbance at 280 nm was measured using a spectrophotometer. From the obtained value, the extinction coefficient calculated by the PACE method was used to calculate the antibody concentration (Protein Science 1995; 4: 2411-2423).

Reference Example 2

Evaluation of FcγR Binding

Binding to FcγR was measured using any of the methods below.

Method Using Protein A

Analysis of the interaction between an antibody and the Fcγ receptor was carried out using BIACORE® T100 system (GE Healthcare). HBS-EP+ (GE Healthcare) was used as the running buffer, and the temperature at measurement was set to 20° C. Protein A (Invitrogen) was immobilized by the amine coupling method, and an antibody of interest was captured onto protein A. After the antibody was captured, Fcγ receptor diluted with the running buffer was allowed to interact for two minutes at a flow rate of 10 μL/min. The amount bound to an antibody was measured, and compared among the antibodies. However, since the amount of Fcγ receptor bound depends on the amount of antibody captured, the amount of Fcγ receptor bound was corrected so that the amount captured by each antibody became 2000 RU (resonance unit). Furthermore, 10 mM glycine-HCl (pH: 1.5) was reacted at a flow rate of 30 μL/min for 30 seconds, and the antibody captured onto the chip was regenerated and used repeatedly.

Method Using Protein L

Analysis of the interaction between an antibody and the Fcγ receptor was carried out using BIACORE® T100 (GE Healthcare). HBS-EP+ (GE Healthcare) was used as the running buffer, and the temperature at measurement was set to 25° C. Protein L (ACTIGEN) was immobilized by the amine coupling method, and an antibody of interest were captured onto protein L. This was interacted with Fcγ receptor diluted in the running buffer for three minutes at a flow rate of 5 μL/min. The amount bound to an antibody was measured, and compared among the antibodies. However, since the amount of Fcγ receptor bound depends on the amount of antibody captured, the amount of Fcγ receptor bound was corrected so that the amount captured by each antibody became 100 RU. Furthermore, 10 mM glycine-HCl (pH: 1.5) was reacted at a flow rate of 30 μL/min for 30 seconds, and the antibody captured onto the chip was washed. The chip was regenerated and used repeatedly.

INDUSTRIAL APPLICABILITY

The present invention provides antibody constant regions that are suitable as pharmaceuticals, wherein the physical properties (stability and homogeneity), antigenicity, safety, and retention in blood have been improved by altering the amino acid sequence of the antibody constant region.

REFERENCES

1. Non-patent Document: Expert Rev. Clin. Innunol. 5, 499-521, 2009.
2. Non-patent Document: Curr. Opin. Drug Discov. Devel. 13, 124-135, 2010.
3. Non-patent Document: Eur J Immunol, 23, 1098-1104, 1993.
4. Non-patent Document: Curr. Opin. 20, 1-7, 2009.
5. Patent Document: PCT/JP2008/067534 (WO2009/041643).
6. Non-patent Document: Blood. 113, 3716-3725, 2009.
7. Non-patent Document: Trends Immunol. 22, 510-6, 2001.

The invention claimed is:

1. A polypeptide comprising the amino acid sequence of SEQ ID NO: 14, wherein the polypeptide is not an antibody.

2. An antibody comprising the amino acid sequence of SEQ ID NO: 14, wherein the antibody further comprises a heavy chain variable region and a light chain variable region, the heavy chain variable region and the light chain variable region each comprising three complementarity determining regions (CDRs).

* * * * *

UNITED STATES PATENT AND TRADEMARK OFFICE
CERTIFICATE OF CORRECTION

PATENT NO. : 10,435,458 B2
APPLICATION NO. : 13/582073
DATED : October 8, 2019
INVENTOR(S) : Taichi Kuramochi et al.

Page 1 of 1

It is certified that error appears in the above-identified patent and that said Letters Patent is hereby corrected as shown below:

In the Specification

Column 34, Line 67: Delete "QuikChange" and insert -- QUIKCHANGE® --, therefor.

Column 35, Line 11: Delete "MILLEX(R)-GV" and insert -- MILLEX®-GV --, therefor.

Column 35, Line 12: Delete "MILLEX(R)-GV" and insert -- MILLEX®-GV --, therefor.

Column 35, Line 15: Delete "Sepharose TM" and insert -- SEPHAROSE™ --, therefor.

Column 36, Line 8: After "BIACORE® T100" insert -- system --, therefor.

Signed and Sealed this
Tenth Day of December, 2019

Andrei Iancu
*Director of the United States Patent and Trademark Office*